(12) United States Patent
Zhang et al.

(10) Patent No.: US 8,983,024 B2
(45) Date of Patent: *Mar. 17, 2015

(54) TETRAHEDRON BEAM COMPUTED TOMOGRAPHY WITH MULTIPLE DETECTORS AND/OR SOURCE ARRAYS

(75) Inventors: Tiezhi Zhang, Troy, MI (US); Xiaochao Xu, Royal Oak, MI (US); Joshua Kim, Royal Oak, MI (US); Di Yan, Auburn Hills, MI (US); Alvaro Martinez, Bloomfield Hills, MI (US)

(73) Assignee: William Beaumont Hospital, Royal Oak, MI (US)

( * ) Notice: Subject to any disclaimer, the term of this patent is extended or adjusted under 35 U.S.C. 154(b) by 332 days.

This patent is subject to a terminal disclaimer.

(21) Appl. No.: 13/194,215

(22) Filed: Jul. 29, 2011

(65) Prior Publication Data

US 2012/0163531 A1 Jun. 28, 2012

Related U.S. Application Data

(63) Continuation-in-part of application No. 12/803,480, filed on Jun. 29, 2010, now Pat. No. 8,611,490, which is a continuation of application No. 11/786,781, filed on Apr. 12, 2007, now Pat. No. 7,760,849.

(60) Provisional application No. 60/792,207, filed on Apr. 14, 2006.

(51) Int. Cl.
*A61B 6/03* (2006.01)
*G21K 1/02* (2006.01)
(Continued)

(52) U.S. Cl.
CPC .............. *G21K 1/025* (2013.01); *A61B 6/025* (2013.01); *A61B 6/032* (2013.01); *A61B 6/06* (2013.01);
(Continued)

(58) Field of Classification Search
CPC ........ A61B 6/025; A61B 6/06; A61B 6/4007; A61B 6/4028; A61B 6/4064; A61B 6/4066; A61B 6/46; A61B 6/032; A61B 6/027; A61B 6/4441; A61B 6/4488; G21K 1/025; G21K 1/02; H01G 1/70; H01J 2235/062; H01J 2235/068
USPC ...................... 378/4, 9, 11, 12, 14, 16, 21, 22
See application file for complete search history.

(56) References Cited

U.S. PATENT DOCUMENTS

| 3,778,614 A | 12/1973 | Hounsfield |
| 3,780,291 A | 12/1973 | Stein et al. |

(Continued)

FOREIGN PATENT DOCUMENTS

| CN | 1419891 | 5/2003 |
| CN | 1589744 A | 3/2005 |

(Continued)

OTHER PUBLICATIONS

Kim, L., et al., "Volumetric Modulated Arc Therapy Using a Rotating Couch: An Accelerated Partial Breast Irradiation Planning Study," Int. L. Radiation Oncology Biol Phys., vol. 75, Issue 3, Supplement 1, Nov. 1, 2009, pp. S732-S733.

(Continued)

*Primary Examiner* — Glen Kao
(74) *Attorney, Agent, or Firm* — Honigman Miller Schwartz and Cohn LLP; Douglas H. Siegel; Jonathan P. O'Brien

(57) ABSTRACT

A tetrahedron beam computed tomography system including an x ray source array that sequentially emits a plurality of x ray beams at different positions along a scanning direction and a collimator that intercepts the plurality of x-ray beams so that a plurality of fan-shaped x-ray beams emanate from the collimator towards an object. The system includes a first detector receiving a first set of fan-shaped x ray beams after they pass through the object, the first detector generating a first imaging signal for each of the received first set of fan-shaped x-ray beams and a second detector receiving a second set of fan-shaped x ray beams after they pass through the object, the second detector generating a second imaging signal for each of the received second set of fan-shaped x-ray beams. Each detector and source pair form a tetrahedral volume. In other embodiments, the system may also have more than two detectors arrays and/or more than one source array. Each pair of source array and detector array forms a tetrahedral volume. Using multiple detector arrays and source arrays can increase field of view, reduce the length of detector and source arrays so that the imaging system is more compact and mobile.

69 Claims, 7 Drawing Sheets

US 8,983,024 B2

Page 2

(51) Int. Cl.
*A61B 6/02* (2006.01)
*A61B 6/06* (2006.01)
*A61B 6/00* (2006.01)
*H05G 1/70* (2006.01)

(52) U.S. Cl.
CPC ............ *A61B 6/4007* (2013.01); *A61B 6/4028* (2013.01); *A61B 6/4064* (2013.01); *A61B 6/4266* (2013.01); *A61B 6/466* (2013.01); *A61B 6/4441* (2013.01); *A61B 6/4488* (2013.01); *G21K 1/02* (2013.01); *H05G 1/70* (2013.01); *H01J 2235/062* (2013.01); *H01J 2235/068* (2013.01); *A61B 6/027* (2013.01)
USPC ........... 378/4; 378/9; 378/19; 378/21; 378/22

(56) References Cited

U.S. PATENT DOCUMENTS

| | | | | |
|---|---|---|---|---|
| 4,132,895 | A | 1/1979 | Froggatt | |
| 4,145,613 | A | 3/1979 | Bunch | |
| 4,304,999 | A | 12/1981 | Richey et al. | |
| 4,315,157 | A | 2/1982 | Barnes | |
| 4,380,818 | A | 4/1983 | Pfeiler | |
| 4,389,569 | A | 6/1983 | Hattori et al. | |
| 4,405,745 | A | 9/1983 | Mathis et al. | |
| 4,414,682 | A | 11/1983 | Annis et al. | |
| 4,534,051 | A | 8/1985 | Grady et al. | |
| 4,547,892 | A | 10/1985 | Richey et al. | |
| 4,712,226 | A | 12/1987 | Horbaschek | |
| 4,920,552 | A | 4/1990 | Hermens | |
| 5,039,867 | A | 8/1991 | Nishihara et al. | |
| 5,125,012 | A | 6/1992 | Schittenhelm | |
| 5,157,707 | A | 10/1992 | Ohlson | |
| 5,214,686 | A | 5/1993 | Webber | |
| 5,335,255 | A | 8/1994 | Seppi et al. | |
| 5,379,333 | A | 1/1995 | Toth | |
| 5,394,452 | A | 2/1995 | Swerdloff et al. | |
| 5,411,026 | A | 5/1995 | Carol | |
| 5,485,494 | A | 1/1996 | Williams et al. | |
| 5,521,957 | A | 5/1996 | Hansen | |
| 5,533,082 | A | 7/1996 | Gronemeyer | |
| 5,602,892 | A | 2/1997 | Llacer | |
| 5,625,661 | A | 4/1997 | Oikawa | |
| 5,657,364 | A | 8/1997 | Pfoh | |
| 5,661,773 | A | 8/1997 | Swerdloff et al. | |
| 5,663,995 | A | 9/1997 | Hu | |
| 5,675,625 | A | 10/1997 | Rockseisen | |
| 5,699,805 | A | 12/1997 | Seward et al. | |
| 5,719,914 | A | 2/1998 | Rand et al. | |
| 5,724,400 | A | 3/1998 | Swerdloff | |
| 5,748,700 | A | 5/1998 | Shepherd et al. | |
| 5,751,781 | A | 5/1998 | Brown et al. | |
| 5,754,622 | A | 5/1998 | Hughes | |
| 5,835,558 | A | 11/1998 | Maschke | |
| 5,848,126 | A | 12/1998 | Fujita et al. | |
| 5,864,597 | A | 1/1999 | Kobayashi | |
| 5,877,501 | A | 3/1999 | Ivan et al. | |
| 5,912,943 | A | 6/1999 | Deucher et al. | |
| 5,929,449 | A | 7/1999 | Huang | |
| 5,949,811 | A | 9/1999 | Baba et al. | |
| 5,966,422 | A | 10/1999 | Dafni et al. | |
| 5,999,587 | A | 12/1999 | Ning et al. | |
| 6,031,888 | A | 2/2000 | Ivan et al. | |
| 6,041,097 | A | 3/2000 | Roos et al. | |
| 6,113,264 | A | 9/2000 | Watanabe | |
| 6,148,058 | A | 11/2000 | Dobbs | |
| 6,152,598 | A | 11/2000 | Tomisaki et al. | |
| 6,200,024 | B1 | 3/2001 | Negrelli | |
| 6,229,870 | B1 | 5/2001 | Morgan | |
| 6,256,370 | B1 | 7/2001 | Yavuz | |
| 6,259,766 | B1 | 7/2001 | Cuppen | |
| 6,269,143 | B1 | 7/2001 | Tachibana | |
| 6,285,739 | B1 | 9/2001 | Rudin et al. | |
| 6,292,534 | B1 | 9/2001 | Linders et al. | |
| 6,307,914 | B1 | 10/2001 | Kunieda et al. | |
| 6,318,892 | B1 | 11/2001 | Suzuki et al. | |
| 6,325,537 | B1 | 12/2001 | Watanabe | |
| 6,345,114 | B1 | 2/2002 | Mackie et al. | |
| 6,385,286 | B1 | 5/2002 | Fitchard et al. | |
| 6,385,288 | B1 | 5/2002 | Kanematsu | |
| 6,389,104 | B1 | 5/2002 | Bani-Hashemi et al. | |
| 6,393,096 | B1 | 5/2002 | Carol et al. | |
| 6,435,715 | B1 | 8/2002 | Betz et al. | |
| 6,463,122 | B1 | 10/2002 | Moore | |
| 6,546,073 | B1 | 4/2003 | Lee | |
| 6,560,311 | B1 | 5/2003 | Shepard et al. | |
| 6,582,121 | B2 | 6/2003 | Crain et al. | |
| 6,618,466 | B1 | 9/2003 | Ning | |
| 6,628,745 | B1 | 9/2003 | Annis et al. | |
| 6,633,627 | B2 | 10/2003 | Horiuchi | |
| 6,661,870 | B2 | 12/2003 | Kapatoes et al. | |
| 6,707,876 | B2 | 3/2004 | Tanigawa | |
| 6,760,402 | B2 | 7/2004 | Ghelmansarai | |
| 6,792,074 | B2 | 9/2004 | Erbel et al. | |
| 6,842,502 | B2 | 1/2005 | Jaffray et al. | |
| 6,865,254 | B2 | 3/2005 | Nafstadius | |
| 6,888,919 | B2 | 5/2005 | Graf | |
| 6,907,100 | B2 | 6/2005 | Taguchi | |
| 6,915,005 | B1 | 7/2005 | Ruchala et al. | |
| 6,980,627 | B2 | 12/2005 | Qiu et al. | |
| 6,990,175 | B2 | 1/2006 | Nakashima et al. | |
| 6,993,112 | B2 | 1/2006 | Hesse | |
| 7,030,386 | B2 | 4/2006 | Pang et al. | |
| 7,062,006 | B1 | 6/2006 | Pelc et al. | |
| 7,072,436 | B2 | 7/2006 | Pelc | |
| 7,127,035 | B2 | 10/2006 | Anno et al. | |
| 7,145,981 | B2 | 12/2006 | Pelc | |
| 7,154,991 | B2 | 12/2006 | Earnst | |
| 7,170,975 | B2 | 1/2007 | Distler et al. | |
| 7,193,227 | B2 | 3/2007 | Hiramoto | |
| 7,227,923 | B2 | 6/2007 | Edic et al. | |
| 7,227,925 | B1 | 6/2007 | Mansfield et al. | |
| 7,280,631 | B2 | 10/2007 | De Man et al. | |
| 7,305,063 | B2 | 12/2007 | Heuscher | |
| 7,388,940 | B1 | 6/2008 | De Man et al. | |
| 7,428,292 | B2 | 9/2008 | De Man et al. | |
| 7,471,765 | B2 | 12/2008 | Jaffray et al. | |
| 7,496,181 | B2 | 2/2009 | Mazin et al. | |
| 7,657,304 | B2 | 2/2010 | Mansfield et al. | |
| 7,760,849 | B2 * | 7/2010 | Zhang | 378/4 |
| 7,826,592 | B2 | 11/2010 | Jaffray et al. | |
| 7,945,021 | B2 | 5/2011 | Shapiro et al. | |
| 8,073,104 | B2 | 12/2011 | Yan et al. | |
| 2003/0072407 | A1 | 4/2003 | Mihara et al. | |
| 2003/0095627 | A1 | 5/2003 | Anderton | |
| 2003/0138077 | A1 | 7/2003 | Lee | |
| 2003/0191363 | A1 | 10/2003 | Boll et al. | |
| 2003/0235271 | A1 | 12/2003 | Rand | |
| 2004/0002641 | A1 | 1/2004 | Sjogren et al. | |
| 2004/0081270 | A1 | 4/2004 | Heuscher | |
| 2004/0086074 | A1 * | 5/2004 | Taguchi | 378/4 |
| 2004/0096033 | A1 | 5/2004 | Seppi et al. | |
| 2004/0120452 | A1 | 6/2004 | Shapiro et al. | |
| 2004/0165696 | A1 | 8/2004 | Lee | |
| 2004/0174949 | A1 | 9/2004 | Yamashita et al. | |
| 2004/0184578 | A1 | 9/2004 | Nakano | |
| 2004/0254448 | A1 | 12/2004 | Amies et al. | |
| 2005/0013404 | A1 | 1/2005 | Kasperl et al. | |
| 2005/0027196 | A1 | 2/2005 | Fitzgerald | |
| 2005/0053189 | A1 | 3/2005 | Gohno et al. | |
| 2005/0054937 | A1 | 3/2005 | Takaoka et al. | |
| 2005/0058237 | A1 | 3/2005 | Morf | |
| 2005/0080336 | A1 | 4/2005 | Byrd et al. | |
| 2005/0085710 | A1 | 4/2005 | Earnst et al. | |
| 2005/0111610 | A1 | 5/2005 | De Man et al. | |
| 2005/0111616 | A1 | 5/2005 | Li et al. | |
| 2005/0111621 | A1 | 5/2005 | Riker et al. | |
| 2005/0197564 | A1 | 9/2005 | Dempsey | |
| 2005/0234327 | A1 | 10/2005 | Saracen | |
| 2005/0249432 | A1 | 11/2005 | Zou | |
| 2005/0251029 | A1 | 11/2005 | Khamene et al. | |
| 2006/0002506 | A1 | 1/2006 | Pelc | |
| 2006/0008047 | A1 | 1/2006 | Zhou et al. | |
| 2006/0017009 | A1 | 1/2006 | Rink et al. | |

(56) References Cited

U.S. PATENT DOCUMENTS

| | | | |
|---|---|---|---|
| 2006/0239409 A1 | 10/2006 | Levene et al. | |
| 2006/0245543 A1 | 11/2006 | Earnst et al. | |
| 2006/0259282 A1 | 11/2006 | Failla et al. | |
| 2006/0269049 A1 | 11/2006 | Yin et al. | |
| 2006/0274885 A1 | 12/2006 | Wang et al. | |
| 2006/0285639 A1 | 12/2006 | Olivera et al. | |
| 2006/0285640 A1 | 12/2006 | Nizin et al. | |
| 2006/0285841 A1 | 12/2006 | Masui | |
| 2007/0003123 A1 | 1/2007 | Fu et al. | |
| 2007/0016014 A1 | 1/2007 | Hara et al. | |
| 2007/0019782 A1 | 1/2007 | Van Stevendaal et al. | |
| 2007/0053492 A1 | 3/2007 | Kidani et al. | |
| 2007/0076846 A1 | 4/2007 | Ruchala et al. | |
| 2007/0280408 A1 | 12/2007 | Zhang | |
| 2008/0031406 A1 | 2/2008 | Yan | |
| 2009/0135994 A1* | 5/2009 | Yu et al. | 378/5 |
| 2010/0008467 A1 | 1/2010 | Dussault et al. | |
| 2010/0054410 A1 | 3/2010 | Nord et al. | |
| 2010/0119032 A1 | 5/2010 | Yan et al. | |
| 2010/0135454 A1 | 6/2010 | Noo | |
| 2011/0002439 A1 | 1/2011 | Zhang et al. | |
| 2011/0080992 A1 | 4/2011 | Dafni | |
| 2011/0211666 A1 | 9/2011 | Ying et al. | |
| 2013/0142310 A1 | 6/2013 | Fahimlan et al. | |

FOREIGN PATENT DOCUMENTS

| | | |
|---|---|---|
| CN | 1723743 A | 1/2006 |
| CN | 1748217 | 3/2006 |
| CN | 1758876 | 4/2006 |
| DE | 1992708 U | 8/1968 |
| DE | 28 22 241 A1 | 12/1978 |
| EP | 0314231 A2 | 5/1989 |
| EP | 0922943 A2 | 6/1999 |
| JP | 52-52594 A | 4/1977 |
| JP | 56-101579 A | 8/1981 |
| JP | 56-168578 A | 12/1981 |
| JP | 58094835 A | 6/1983 |
| JP | 4242736 A | 8/1992 |
| JP | 4-307035 A1 | 10/1992 |
| JP | 5-172764 A | 7/1993 |
| JP | 07255717 A | 10/1995 |
| JP | 8122438 A | 5/1996 |
| JP | 09-218939 A | 8/1997 |
| JP | 9327453 A | 12/1997 |
| JP | 10-033520 A | 2/1998 |
| JP | 10113400 A | 5/1998 |
| JP | 10511595 A | 11/1998 |
| JP | 10328318 A | 12/1998 |
| JP | 11-047290 | 2/1999 |
| JP | 1199148 A | 4/1999 |
| JP | 11160440 A | 6/1999 |
| JP | 11-276463 | 10/1999 |
| JP | 2000126164 A | 5/2000 |
| JP | 2000176029 A | 6/2000 |
| JP | 2000308634 A | 11/2000 |
| JP | 2002210028 A | 7/2002 |
| JP | 2003210596 A | 7/2003 |
| WO | 9713552 A1 | 4/1997 |
| WO | 9852635 A1 | 11/1998 |
| WO | 9903397 A1 | 1/1999 |
| WO | WO0160236 A | 8/2001 |
| WO | WO2004061744 A2 | 7/2004 |
| WO | WO2004061864 A2 | 7/2004 |
| WO | WO2004080309 A2 | 9/2004 |
| WO | WO2006/018761 A1 | 2/2006 |
| WO | WO2006034973 A1 | 4/2006 |

OTHER PUBLICATIONS

Nakagawa, K. et al., "Development of a megavoltage ct scanner using linear accelerator treatment beam", Journal of JASTRO, vol. 3, No. 4, pp. 265-276, 1991, Japanese Society for Therapeutic Radiology and Oncology.

Shirato, H., "Real-time tumor tracking radiotherapy and stereotactic irradiation", Monthly New Medical Care, vol. 26, No. 12, pp. 61-63, 1999, ME Co., Ltd.

Violni F et al. "NSABP/RTOG 0413: A randomized phase III study of conventional whole breast irradiation versus partial breast irradiation for women with Stage 0, I, or II breast cancer" Mar. 13, 2007.

Hepel, Jaroslaw T. et al. "Toxicity of three-dimensional conformal radiotherapy for accelerated partial breast irradiation" Int. J. Radiat. Oncol. Biol. Phys., vol. 75, No. 5, 2009, pp. 1290-1296.

Jagsi Reshma et al. "Unacceptable cosmesis in a protocol investigating intensity modulated radiotherapy with active breathing control for accelerated partial breast irradiation" Int. J. Radiat. Oncol. Biol. Phys. Vo. 76, No. 1, 2009, pp. 71-78.

Livi, Lorenzo et al. "Accelerated partial breast irradiation with IMRT: new technical approach and interim analysis of acute toxicity in a phase III randomized clinical trial" Int. J. Radiat. Oncol. Biol. Phys. vol. 77, No. 2, 2010, pp. 509-515.

Smith, Benjamin D., et al., "Accelerated partial breast irradiation consensus statement from the american society for radiation oncology (ASTRO)," Int. J. Radiat. Oncol. Biol. Phys., vol. 74, No. 4, 2009, pp. 987-1001.

Veronesi, Umberto, et al., "Twenty year follow-up of a randomized study comparing breast-conserving surgery with radical mastectomy for early breast cancer," N. Engl. J. Med., vol. 347, No. 16, Oct. 17, 2002, pp. 1227-1232.

Jain, Anudh K., et al., "Does three-dimensionai external beam partial breast irradiation spare lung tissue compared with standard whole breast irradiation?" Int. Radiat. Oncol. Biol. Phys., vol. 75, No. 1, 2009, pp. 82-88.

Recht, Abram, et al., "Lung dose-volume parameters and the risk of pneumonitis for patients treated with accelerated partial-breast irradiation using three-dimensional conformal radiotherapy," J. Clin. Oncol., vol. 27, No. 24, Aug. 20, 2009, pp. 3887-3893.

Low, Jennifer A, et al., "Long-term follow-up for locally advanced and inflammatory breast cancer patients treated with multimodality therapy," J. Clin. Oncol., vol. 22, No. 20, Oct. 15, 2004, pp. 4067-4074.

Romond, Edward H., et al., "Trastuzumab plus adjuvant chemotherapy for operable HER2-positive breast cancer," N. Engl. J. Med., vol. 353, No. 16, Oct. 20, 2005, pp. 1673-1684.

Piccart-Gebhart, Martine J., et al., "Trastuzumab after adjuvant chemotherapy in HER2-positive breast cancer," N. Engl. J. Med., vol. 353, No. 16, Oct. 20, 2005, pp. 1659-1672.

Berrington de Gonzalez, A., et al., "Second solid cancers after radiotherapy for breast cancer in SEER cancer registries," Br. J. Cancer 2009, vol. 102, No. 1, Jan. 5, 2010, pp. 220-226.

Stovall, Marilyn, et al., "Dose to the contralateral breast from radiotherapy and risk of second primary breast cancer in the WECARE study," Int. J. Radiat. Oncol. Biol. Phys., vol. 72, No. 4, 2008, pp. 1021-1030.

Kozak, Kevin R, et al., "Dosimetric comparison of two different three-dimensional conformanl external beam accelerated partial breast irradiation techniques," Int. J. Radiat. Oncol. Biol. Phys., vol. 65, No. 2, 2006, pp. 340-346.

Rusthoven, Kyle E., et al., "Accelerated partial-breast intensity-modulated radiotherapy results in improved dose distribution when compared with three-dimensional treatment-planning techniques," Int. J. Radiat. Oncol. Biol. Phys., vol. 70, No. 1, 2008, pp. 296-302.

Moran, Jean M., et al., "Accelerated partial breast irradiation: what is dosimetric effect of advanced technology approaches?," Int. J. Radiat. Oncol. Biol. Phys., vol. 75, No. 1, 2009, pp. 294-301.

Wernicke, A.G., et al., "External beam partial breast irradiation following breast-conserving surgery: preliminary results of cosmetic outcome of NYU 00-23," Int. J. Radiat. Oncol. Biol. Phys. vol. 66, No. 3, Supplement, 2006, p. S32.

Formenti, Silvia C., et al., "Prone accelerated partial breast irradiation after breast-conserving surgery: preliminary clinical results and dose-volume histogram analysis," Int. J. Radiat. Oncol. Biol. Phys., vol. 60, No. 2, 2004, pp. 493-504.

Kozak, Kevin R., et al., "Dosimetric comparison of proton and photon three-dimensional, conformal, external beam accelerated partial breast irradiation techniques," Int. J. Radiat. Oncol. Biol. Phys., vol. 65, No. 5, 2006, pp. 1572-1578.

(56) References Cited

OTHER PUBLICATIONS

Yu CX., "Intensity-modulated arc therapy with dynamic multileaf collimation: an alternative to tomotherapy," Phys. Med. Biol., vol. 40, 1995. pp. 1435-1449.

Yu, Cedric X., et al., "Clinical implementation of intensity-modulated arc therapy," Int. J. Radiat. Oncol. Biol. Phys., vol. 53, No. 2, 2002, pp. 453-463.

Burgess, L., et al., "Partial Brain VMAT Planning Using Simultaneous Couch and Gantry Arcs," Int. L. Radiation Oncology Biol. Phys., vol. 78, Issue 3, Supplement 1, Nov. 1, 2010, pp. S818-S819.

Otto K., "Volumetric modulated arc therapy: IMRT in a single gantry arc," Med. Phys., vol. 35, 2008, pp. 310-317.

Palma, David, et al., Volumetric modulated arc therapy for delivery of prostate radiotherapy: comparison with intensity-modulated radiotherapy and three-dimensional conformal radiotherapy, Int. J. Radiat. Oncol. Biol. Phys., vol. 72, No. 4, 2008, pp. 996-1001.

Duthoy, W., et al., "Clinical implementation of intensity-modulated arc therapy (IMAT) for rectal cancer," Int. J. Radiat. Oncol. Biol. Phys., vol. 60, No. 3, 2004, pp. 794-806.

Lagerwaard FJ., et al., Whole-brain radiotherapy with simultaneous integrated boost to multiple brain metastases using volumetric modulated arc therapy, Int. J. Radiat. Oncol. Biol. Phys., vol. 75, No. 1, 2009, pp. 253-259.

Popescu CC., et al., "Volumetric modulated arc therapy improves dosimetry and reduces treatment time compared to conventional intensity-modulated radiotherapy for locoregional radiotherapy of left-sided breast cancer and internal mammary nodes," Int J Radiat Oncol Biol Phys, vol. 76, No. 1, 2009, pp. 287-295.

Clarke M., et al., "Effects of radiotherapy and of differences in the extent of surgery for early breast cancer on local recurrence and 15-year survival: An overview of the randomised trials," Lancet, vol. 366, 2005, pp. 2087-2106.

Paszat, Lawrence F., et al., "Mortality from myocardial infarction following postlumpectomy radiotherapy for breast cancer: A population-based study in Ontario, Canada," Int J Radiat Oncol Biol Phys, vol. 43, No. 4, 1999, pp. 755-762.

Baglan, Kathy L. et al., "Accelerated partial breast irradiation using 3D conformal radiation therapy (3D-CRT)," Int J Radiat Oncol Biol Phys, vol. 55, No. 2, 2003, pp. 302-311.

Pignol, Jean-Philippe, et al., "A multicenter randomized trial of breast intensity-modulated radiation therapy to reduce acute radiation dermatitis," J Clin Oncol, vol. 26, No. 13, May 1, 2008, pp. 2085-2092.

Reeder, Reed, et al., "Predictions for clinical outcomes after accelerated partial breast intensity-modulated radiotherapy," Int J Radiat Oncol Biol Phys, vol. 74, No. 1, 2009, pp. 92-97.

Hall, Eric J., et al., "Radiation-induced second cancers: The impact of 3D-CRT and IMRT," Int J Radiat Oncol Biol Phys. vol. 56, No. 1, 2003, pp. 83-88.

Shaitelman, Simona F., et al., "Continuous Arc Rotation of the Couch Therapy for the Delivery of Accelerated Partial Breast Irradiation: A Treatment Planning Analysis," Int. J. Radiation Oncology Biol. Phys., vol. 80, No. 3. 2011, pp. 771-778.

Takahashi, S., "Conformation Radiotherapy. Rotation Techniques as Applied to Radiography and Radiotherapy of Cancer," Acta Radiol, Diagn (Stockh), Suppl 242:1+, 1965, pp. 11-140.

U.S. Appl. No. 11/805,716, filed May 24, 2007, Di Yan et al.

U.S. Appl. No. 12/803,480, filed Jun. 29, 2010, Tiezhi Zhang.

Zhang, J., et al., "A Multi-Beam X-Ray Imaging System Based on Carbon Nanotube Field Emitters," Medical Imaging 2006: Physics of Medical Imaging Proceedings of SPIE, vol. 6142, (2006), eight pages.

Schmidt, T.G., et al., "A Prototype Table-Top Inverse-Geometry Volumetric CT Images," Med. Phys. vol. 33, No. 6 (Jun. 2006) pp. 1867-1878.

Shihaliev, P.M., et al., "Photon Counting Computed Tomography: Concept and Initial Results," source unknown, date unknown, one page.

Webb, S., et al., Abstract of "Monte Carlo Modelling of the Performance of a Rotating Slit-collimator for Improved Planar Gamma-Camera Imaging," source unknown, date unknown, one page.

Gupta, N.K., et al., "Tangential CT, A Computed Tomography Method Developed for Industrial Inspection," source unknown, date unknown, five pages.

Zeng. G.L., et al., "Image Reconstruction Algorithm for a SPECT System with a Convergent Rotating Slat Collimator," source unknown, date unknown, four pages.

European Search Report for Application No. 07755309.7 dated Apr. 15, 2011.

Antonuk, L.E., et al., "A Real-Time, Flat-Panel, Amorphous Silicon, Digital X-Ray Imager", Radiographics, vol. 15, No. 4, Jul. 1995, pp. 993-1000.

Antonuk, L.E., et al., "Initial Performance Evaluation of an Indirect-Detection, Active Matrix Flat-Panel Imager (AMFPI) Prototype for Megavoltage Imaging", Int. J. Radiat. Oncol. Biol. Phys., vol. 42, No. 2, 1998, pp. 437-454.

Antonuk, L.E., et al., "Megavoltage Imaging with a Large-Area, Flat-Panel, Amorphous Silicon Imager", Int. J. Radiat. Oncol. Biol. Phys., vol. 36, No. 3, 1996, pp. 661-672.

Antonuk, L.E., et al., "Strategies to Improve the Signal and Noise Performance of Active Matrix, Flat-Panel Imagers for Diagnostic X-Ray Applications", Med. Phys., vol. 27, No. 2, Feb. 2000, pp. 289-306.

Basset, P.G., Wong, J.W. and Aspin, N.: "An Interactive Computer System for Studying Human Mucociliary Clearance", Computer Biol. Med. 1979, vol. 9, pp. 97-105.

Birkner, M., et al., "Adapting Inverse Planning to Patient and Organ Geometrical Variation: Algorithm and Implementation," Med. Phys., vol. 30, No. 10, Oct. 2003, pp. 2822-2831.

Bissonnette, J.P., et al., "Optimal Radiographic Magnification for Portal Imaging.", Med. Phys., vol. 21, No. 9, Sep. 1994, pp. 1435-1445.

Boyer, A.L., et al., (IMRT Collaborative Working Group): "Intensity-modulated radiotherapy: Current status and issues of interest", Int. J. Radiat. Oncol. Biol. Phys. 2001, vol. 51, No. 4, pp. 880-914.

Boyer, A.L., et al., "A Review of Electronic Portal Imaging Devices (EPIDs)", Medical Physics, Jan./Feb. 1992, vol. 19, No. 1, pp. 19: 1-16.

Brown, A.P., et al., "Three-Dimensional Photon Treatment Planning for Hodgkin's Disease", Int. J. Radiat. Oncol. Biol. Phys., May 15, 1991, vol. 21, No. 1, pp. 205-215.

Chen, J., et al., "Dose-Guided Radiation Therapy with Megavoltage Cone-Beam CT," published by the British Journal of Radiology, vol. 79, 2006, pp. S87-S98.

Cheng, A., et al., "Systematic Verification of a Three-Dimensional Electron Beam Dose Calculation Algorithm", Med. Phys., 1996, vol. 23, No. 5, pp. 685-693.

Chi, Y., et al., "A Material Sensitivity Study on the Accuracy of Deformable Organ Registration Using Linear Biomechanical Models," Med. Phys., vol. 33: No. 2, Feb. 2006, pp. 421-433.

Cullity, B.D., "Elements of X-Ray Diffraction, Second Edition," (Reading, MA: Addison Wesley, 1978), p. 6-12.

Dieu, L., et al., "Ion Beam Sputter-Deposited SiN/TiN Attenuating Phase-Shift Photoblanks," publication source and date unknown, 8 pages.

Drake, D.G., et al., "Characterization of Fluoroscopic Imaging System for kV and MV Radiography", Med. Phys., May 2000, vol. 27, No. 5, pp. 898-905.

Du, M.N., et al., "A Multileaf Collimator Field Prescription Preparation System for Conventional Radiotherapy", Int. J. Radiat. Oncol. Biol. Phys., 1994, vol. 30, No. 3, pp. 707-714.

Du, M.N., et al, "A Multileaf Collimator Field Prescription Preparation System for Conventional Radiotherapy", Int. J. Radiat. Oncol. Biol. Phys., 1995, vol. 32, No. 2, pp. 513-520.

El-Mohri, Y., et al., "Relative Dosimetry Using Active Matrix Flat-Panel Imager (AMFPI) Technology", Med. Phys., Aug. 1999, vol. 26, No. 8, pp. 1530 -1541.

Ezz, A., et al, "Daily Monitoring and Correction of Radiation Field Placement Using a Video-Based Portal Imaging System: a Pilot Study", Int. J. Radiat. Oncol. Biol. Phys., 1992, vol. 22, No. 1, pp. 159-165.

(56) References Cited

OTHER PUBLICATIONS

Frazier, A., et al., "Dosimetric Evaluation of the Conformation of the Multileaf Collimator to Irregularly Shaped Fields", Int. J. Radiat. Oncol.Biol. Phys., 1995, vol. 33, No. 5, pp. 1229-1238.

Frazier, A., et al., "Effects of Treatment Setup Variation on Beam's Eye View Dosimetry for Radiation Therapy Using the Multileaf Collimator vs. The Cerrobend Block", Int. J. Radiat. Oncol. Biol. Phys., 1995, vol. 33, No. 5, pp. 1247-1256.

Ghilezan, M., et al., "Online Image-Guided Intensity-Modulated Radiotherapy for Prostate Cancer: How Much Improvement Can We Expect? A Theoretical Assessment of Clinical Benefits and Potential Dose Escalation by Improving Precision and Accuracy of Radiation Delivery," Int. J. Radiation Oncology Biol. Phys., vol. 60, No. 5, 2004, pp. 1602-1610.

Graham, M.L., et al., "A Method to Analyze 2-Dimensional Daily Radiotherapy Portal Images from an On-Line Fiber-Optic Imaging System.", Int. J. Radiat. Oncol. Biol. Phys., Mar. 1991, vol. 20, No. 3, pp. 613-619.

Halverson, K.J., et al, "Study of Treatment Variation in the Radiotherapy of Head and Neck Tumors Using a Fiber-Optic On-Line Line Radiotherapy Imaging System", Int. J. Radiat. Oncol. Biol. Phys., Oct. 1991, vol. 21, No. 5, pp. 1327-1336.

Harms, W.B., Sr., et al., "A Software Tool for the Quantitative Evaluation of 3D Dose Calculation Algorithms", Med. Phys., Oct. 1998, vol. 25, No. 10, pp. 1830-1839.

Herman, M.G., et al. "Clinical use of electronic portal imaging: Report of AAPM Radiation Therapy Committee Task Group 58", Med. Phys. May 2001, vol. 28, No. 5, pp. 712-737.

International Search Report for PCT/US2007/008996, dated Mar. 4, 2008, three pages.

Jaffray, et al., Cone-Beam CT: Applications in Image-Guided External Beam Radiotherapy and Brachytherapy, publication source unknown, date unknown, one page.

Jaffray, et al., "Conebeam Tomographic Guidance of Radiation Field Placement for Radiotherapy of the Prostate," Manuscript accepted for publication in the International Journal of Radiation Oncology, Biology, Oct. 1998, 32 pages.

Jaffray, et al., "Exploring 'Target of the Day' Strategies for a Medical Linear Accelerator with Conebeam-CT Scanning Capability," XIIth ICCR held in Salt Lake City, Utah, May 27-30, 1997, pp. 172-174.

Jaffray, et al., "Flat-Panel Cone-Beam CT for Image-Guided External Beam Radiotherapy," publication source unknown, Oct. 1999, 36 pages.

Jaffray, et al., "Managing Geometric Uncertainty in Conformal Intensity-Modulated Radiation Therapy," Seminars in Radiation Oncology, vol. 9, No. 1, Jan. 1999 pp. 4-19.

Jaffray, et al., "Performance of a Volumetric CT Scanner Based Upon a Flat-Panel Imager," SPIE Physics of Medical Imaging, vol. 3659, Feb. 1999, pp. 204-214.

Jaffray, D.A., et al., "A Radiographic and Tomographic Imaging System Integrated into a Medical Linear Accelerator for Localization of Bone and Soft-Tissue Targets", Int. J. Radiat. Oncol. Biol. Phys., 1999, vol. 45, No. 3, pp. 773-789.

Jaffray, D.A., et al., "Activity Distribution of a Cobalt-60 Teletherapy Source", Med. Phys., Mar./Apr. 1991, vol. 18, No. 2, pp. 288-291.

Jaffray, D.A., et al., "Cone-Beam Computed Tomography with a Flat-Panel Imager: Initial Performance Characterization", Med. Phys. Jun. 2000, vol. 27, No. 6, pp. 1311-1323.

Jaffray, et al., "Cone-Beam Computed Tomography with a Flat-Panel Imager: Initial Performance Characterization," Submission to the Medical Physics Journal for publication on Aug. 1999, 36 pages.

Jaffray, D.A., et al., "Dual-Beam Imaging for Online Verification of Radiotherapy Field Placement", Int. J. Radiat. Oncol. Biol. Phys., 1995, vol. 33, No. 5, pp. 1273-1280.

Jaffray, D.A., et al., "X-Ray Scatter in Megavoltage Transmission Radiography: Physical Characteristics and Influence on Image Quality", Med. Phys., Jan. 1994, vol. 21, No. 1, pp. 45-60.

Jaffray, D.A., et al., "X-Ray Sources of Medical Linear Accelerators: Focal and Extra-Focal Radiation", Med. Phys. Sep./Oct. 1993, vol. 20, No. 5, pp. 1417-1427.

Kapatoes, J.M., et al., "On the Accuracy and Effectiveness of Dose Reconstruction for Tomotherapy," Phys. Med. Biol., vol. 46, 2001, pp. 943-966.

Kessler, M.L., "Image Registration and Data Fusion in Radiation Therapy," The British Journal of Radiology, vol. 79, 2006, pp. S99-S108.

Kestin, L.L., et al., "Improving the Dosimetric Coverage of Interstitial High-Dose-Rate Breast Implants", Int. J. Radiat. Oncol. Biol. Phys., 2000, vol. 46, No. 1, pp. 35-43.

Kestin, L.L., et al., "Intensity Modulation to Improve Dose Uniformity with Tangential Breast Radiotherapy: Initial Clinical Experience" Int J. Radiat. Oncol. Biol. Phys., 2000, vol. 48, No. 5, pp. 1559-1568.

Kini, V.R., et al., "Use of Three-Dimensional Radiation Therapy Planning Tools and Intraoperative Ultrasound to Evaluate High Dose Rate Prostate Brachytherapy Implants", Int. J. Radiat. Oncol. Biol. Phys., 1999, vol. 43, No. 3, pp. 571-578.

Kress, J., et al. "Patient position verification using CT images" Medical Physics, AIP, 26(6) 1999, 941-948.

Laughlin, J.S., et al., (writing chairs), "Evaluation of High Energy Photon External Beam Treatment Planning: Project Summary", Int. J. Rad. Oncol. Biol. Physics, 1991, vol. 21, pp. 3-8.

Liang, J., et al., "Reducing Uncertainties in Volumetric Image Based Deformable Organ Registration," Med. Phys., vol. 30, No. 8, Aug. 2003, pp. 2116-2122.

Lockman, D., et al., "Estimating the Dose Variation in a Volume of Interest with Explicit Consideration of Patient Geometric Variation," Med. Phys., vol. 27, No. 9, Sep. 2000, pp. 2100-2108.

Lucas, "Analysis of surface dose variation in CT procedures." The British Journal of Radiology, 74 (2001), 1128-1136.

Martinez, A., et al., "Improvement in dose escalation using the process of adaptive radiation therapy combined with three dimensional conformal or Intensity modulated beams for prostate cancer", Int. J. Radiat. Oncol. Biol. Phys. 2001, vol. 50, No. 5, pp. 1226-1234.

Masterson, M.E., et al., "Inter-Institutional Experience in Verification of External Photon Dose Calculations", Int. J. Rad. Oncol. Biol. Physics, 1991, vol. 21, pp. 37-58.

Michalski, J., et al., "An Evaluation of Two Methods of Anatomical Alignment of Radiotherapy Portal Images", Int. J. Radiat. Oncol. Biol. Phys., 1993; vol. 27. No. 5, pp. 1199-1206.

Michalski, J.M., et al., "Prospective Clinical Evaluation of an Electronic Portal Imaging Device", Int. J. Radiat. Oncol. Biol. Phys., 1996, vol. 34, No. 4, pp. 943-951.

Michalski, J.M., et al., "The Use of On-Line Image Verification to Estimate the Variation in Radiation Therapy Dose Delivery", Int. J. Radiat. Oncol. Biol. Phys., 1993, vol. 27, No. 3, pp. 707-716.

Milliken, B.D., et al., "Verification of the Omni Wedge Technique", Med. Phys. Aug. 1998, vol. 25, No. 8, pp. 1419-1423.

Mohan, R. (writing chair), "Three-Dimensional Dose Calculations for Radiation Treatment Planning", Int. J. Rad. Oncol. Biol. Physics, May 15, 1991; vol. 21, No. 1, pp. 25-36.

Mueller, K., et al., "Cone-Beam Computed Tomography (CT) for a Megavoltage Linear Accelerator (LINAC) Using an Electronic Portal Imaging Device (EPID) and the Algebraic Reconstruction Technique (ART)," publication source unknown, (publication date unknown), 4 pages, while the date of publication is unknown, it is believe that the article was publicly available before May 24, 2007.

Oldham, M., et al., "Practical aspects of in situ 160(y,n)150 activation using a conventional medical accelerator for the purpose of perfusion imaging", Med. Phys. Aug. 2001; vol. 28, No. 8, pp. 1669-1678.

Perera, H., et al., "Rapid Two-Dimensional Dose measurement in Brachytherapy Using Plastic Scintillator Sheet: Linearity, Signal-to-Noise Ratio, and Energy Response Characteristics.", Int. J. Radiat. Oncol. Biol. Phys., 1992, vol. 23, No. 5, pp. 1059-1069.

Pisani, L., et al., "Setup Error in Radiotherapy: On-line Correction Using Electronic Kilovoltage and Megavoltage Radiographs", Int. J. Radiat. Oncol. Biol. Phys., 2000, vol. 47, No. 3, pp. 825-839.

Purdy, J.A., et al., "State of the Art High Energy Photon Treatment Planning", Front Radiat. Ther. Oncol., 1987, vol. 21, pp. 4-24.

Schaly, B., et al., "Tracking the Dose Distribution in Radiation Therapy by Accounting for Variable Anatomy," Phys. Med. Biol., vol. 49, 2004, pp. 791-805.

(56) References Cited

OTHER PUBLICATIONS

Sharpe, M.B., et al., "Compensation of X-Ray Beam Penumbra in Conformal Radiotherapy", Med. Phys., Aug. 2000, vol. 27, No. 8, pp. 1739-1745.
Sharpe, M.B., et al., "Monitor Unit Settings for Intensity Modulated Beams Delivered Using a Step-and-Shoot Approach", Med. Phys., Dec. 2000, vol. 27, No. 12, pp. 2719-2725.
Shiu, A.S., et al., "Verification Data for Electron Beam Dose Algorithms", Med. Phys., May/Jun. 1992, vol. 19, No. 3, pp. 623-636.
Siewerdsen, et al., "Cone-Beam CT with a Flat-Panel Imager: Noise Consideration for Fully 3-D Computed Tomography," SPIE Physics of Medical Imaging, vol. 3336, Feb. 2000, pp. 546-554.
Siewerdsen, et al., "Optimization of X-Ray Imaging Geometry (with Specific Application to Flat-Panel Cone-Beam Computed Tomography)," Non-Final Version of Manuscript to be published in Med. Phys., vol. 27, No. 8, Aug. 2000, pp. 1-12.
Siewerdsen, J.H., et al., "A Ghost Story: Spatio-Temporal Response Characteristics of an Indirect-Detection Flat-Panel Imager", Med. Phys., Aug. 1999, vol. 26, No. 8, pp. 1624-1641.
Siewerdsen, et al., "Cone-Beam Computed Tomography with a Flat-Panel Imager: Effects of Image Lag," Med. Phys., vol. 26, No. 12, Dec. 1999, pp. 2635-2647.
Siewerdsen, J.H., et al., "Cone-Beam Computed Tomography with a Flat-Panel Imager: Magnitude and Effects of X-Ray Scatter", Med. Phys., Feb. 2001, vol. 28, No. 2, pp. 220-231.
Siewerdsen, J.H., et al., "Empirical and Theoretical Investigation of the Noise Performance of Indirect Detection, Active Matrix Flat-Panel Imagers (AMFPIs) for Diagnostic Radiology", Med. Phys., Jan. 1997, vol. 24, No. 1, pp. 71-89.
Siewerdsen, J.H., et al., "Optimization of X-Ray Imaging Geometry (with Specific Application to Flat-Panel Cone-Beam Computed Tomography)", Med. Phys., Aug. 2000, vol. 27, No. 8, pp. 1903-1914.
Siewerdsen, JH, et al., "Signal, Noise Power Spectrum, and Detective Quantum Efficiency of Indirect-Detection Flat-Panel Panel Imagers for Diagnostic Radiology", Med. Phys., May 1998, vol. 25, No. 5, pp. 614-628.
Sohn, M. et al., "Modeling Individual Geometric Variation Based on Dominant Eigenmodes of Organ Deformation: Implementation and Evaluation," Phys Med Biol, vol. 50, 2005, pp. 5893-5908.
Sontag, M.R. and Purdy, J.A. (writing chairs), "State of the Art of External Photon Beam Radiation Treatment Planning", Int. J. Rad. Oncol. Biol. Physics. 1991, vol. 21 No. 1, pp. 9-23.
Stromberg, J.S., et al., "Active Breathing Control (ABC) for Hodgkin's Disease: Reduction in Normal Tissue Irradiation with Deep Inspiration and Implications for Treatment", Int. J. Radiat. Oncol. Biol. Phys. 2000, vol. 48, No. 3, pp. 797-806.
Teicher, B.A., et al., "Allosteric Effectors of Hemoglobin as Modulators of Chemotherapy and Radiation Therapy in Vitro and in Vivo", Cancer Chemother. Pharmacol., 1998, vol. 42, pp. 24-30.
Tepper, J.E. and Shank, B. (writing Chairs), "Three-Dimensional Display in Planning Radiation Therapy: A Clinical Perspective", Int. J. Rad. Oncol. Biol. Physics. 1991, vol. 21, No. 1, pp. 79-89.
Urie, M.M., et al., "The Role of Uncertainty Analysis in Treatment Planning", Int. J. Radiat. Oncol. Biol. Phys., 1991, vol. 21, No. 1, pp. 91-107.
Vicini, F.A., et al., "Low-Dose-Rate Brachytherapy as the Sole Radiation Modality in the Management of Patients with Early-Stage Breast Cancer Treated with Breast-Concerving Therapy: Preliminary Results of a Pilot Trial", Int. J. Radiat. Oncol. Biol. Phys., 1997, vol. 38, No. 2, pp. 301-310.
Vicini, F.A., et al., "Dose-Volume Analysis for Quality Assurance of Interstitial Brachytherapy for Breast Cancer", Int. J. Radiat. Oncol. Biol. Phys., 1999, vol. 45, No. 3, pp. 803-810.
Vicini, F.A., et al., "Implementation of a 3D-Virtual Brachytherapy in the Management of Breast Cancer: a Description of a New Method of Interstitital Brachytherapy", Int. J. Radiat. Oncol. Biol. Phys., 1998, vol. 40, No. 3, pp. 629-635.
Weinberg, R., et al., "Dosimetric Uncertainties of Three-Dimensional Dose Reconstruction from Two-Dimensional Data in a Multi-Institutional Study," Journal of Applied Clinical Medical Physics, vol. 5, No. 4, Fall 2004, pp. 15-28.
Williamson, J.F., et al., "One-Dimensional Scatter-Subtraction Method for Brachytherapy Calculation Near Bounded Heterogeneities", Med. Phys., Jan./Feb. 1993, vol. 20, No. 1, pp. 233-244.
Wong, J.K., et al., "Conservative Management of Osteoradionecrosis", Oral Surg. Oral Med. Pahol. Oral Pathol., Jul. 1997, vol. 84, No. 1, pp. 16-21.
Wong, J.W., et al., "Development of a Second-Generation Fiber-Optic On-Line Image Verification System", Int. J. Radiat. Oncol. Biol. Phys., 1993, vol. 26, No. 2, pp. 311-320.
Wong, J.W., et al., "Effect of Small Inhomogeneities on Dose in a Cobalt-60 Beam", Med. Phys., Nov./Dec. 1981, vol. 8, No. 6, pp. 783-791.
Wong, J.W., et al., "On Methods of Inhomogeneity Corrections for Photon Transport", Med. Phys., Sep./Oct. 1990, vol. 17, No. 5, pp. 807-814.
Wong, J.W., et al., "On-Line Image Verification in Radiation Therapy: An Early USA Experience", Med. Prog. Through Technol., 1993, vol. 19, pp. 43-54.
Wong, J.W., et al., "On-Line Radiotherapy Imaging with an Array of Fiber-Optic Image Reducers", Int. J. Radiat. Oncol. Biol. Phys., Jun. 1990, vol. 18, No. 6, pp. 1477-1484.
Wong, J.W., et al., "Portal Dose Images. I: Quantitative Treatment Plan Verification", Int. J. Radiat. Oncol. Biol. Phys., Jun. 1990, vol. 18, No. 6, pp. 1455-1463.
Wong, J.W., et al., "Reconsideration of the Power-Law (Batho) Equation for Inhomogeneity Corrections", Med. Phys., Jul./Aug. 1982, vol. 9, No. 4, pp. 521-530.
Wong, J.W., et al., "Second Scatter Contribution to Dose in Cobalt-60 Beam" Med. Phys., Nov./Dec. 1981, vol. 8, No. 6, pp. 775-782.
Wong, J.W., et al., "The Cumulative Verification Image Analysis Tool for Offline Evaluation of Portal Images", Int. J. Radiat. Oncol. Biol. Phys., 1995, vol. 33, No. 5, pp. 1301-1310.
Wong, J.W., et al., "The Use of Active Breathing Control (ABC) to Reduce Margin for Breathing Motion", Int. J. Radiat. Oncol. Biol. Phys., 1999, vol. 44, No. 4, pp. 911-919.
Wong, J.W., et al., "Treatment Verifications and Patient Dose Estimations Using Portal Dose Imaging" Radiotherapy System Research (Japan). 1988; vol. 5, No. 3, pp. 213-225.
Wong, J.W., et al.; "A New Approach to CT Pixel-Based Photon Dose Calculations in Heterogeneous Media", Med. Phys., Mar./Apr. 1983, vol. 10, No. 2, pp. 199-208.
Wong, J.W., (writing chair), "Role of Inhomogeneity Corrections in 3D Photon Treatment Planning", Int. J. Rad. Oncol. Biol. Physics. 1991, vol. 21, No. 1, pp. 59-69.
Wu, Y., et al., "Implementing multiple static field delivery for intensity modulated beams", Med. Phys., Nov. 2001, vol. 28, No. 11, pp. 2188-2197.
Xu, Xiaochao, et al., "A Tetrahedron Beam Computed Tomography Benchtop System With a Multiple Pixel Field Emission X-Ray Tube," Med. Phys., vol. 3, No. 10, 2001, pp. 5500-5508.
Yan, D., et al., "The influence of interpatient and intrapatient rectum variation on external beam treatment of prostate cancer", Int. J. Radiat. Oncol. Biol. Phys. 2001, vol. 51, No. 4, pp. 1111-1119.
Yan, D., et al., "Organ/Patient Geometric Variation in External Beam Radiotherapy and Its Effect," Med. Phys., vol. 28, No. 4, Apr. 2001, pp. 593-602.
Yan, D., "Adapt Radiotherapy to Temporal Biological Targets Assessed Using Biological Images," publication source unknown, while the date of publication is unknown, it is believe that the article was publicly available before May 24, 2007, 3 pages.
Yan, D., "Image-Guided Adaptive Radiotherapy Model," AAPM, Mar. 10, 2006, pp. 1-15.
Yan, D., "Image-Guided/Adaptive Radiotherapy," Medical Radiology-Radiation Oncology, Volume: New Technologies in Radiation Oncology, Edited by W. Schlegel, T. Bortfeld and AL Grosu, Springer-Verlag, Berlin, Heidelberg, New York, Hong Kong, Sep. 8, 2005, ISBN 3-540-00321-5, pp. 317-332.
Yan, D., "Treatment Strategy for Daily Image Feedback Adaptive Radiotherapy," Proceeding, XIIIth International Conference on the Use of Computers in Radiotherapy, Heidelberg, Germany, 2000, pp. 518-520.

(56) References Cited

OTHER PUBLICATIONS

Yan, D., et al., "A Model to Accumulate Fractionated Dose in a Deforming Organ," Int. J. Radiation Oncology Biol. Phys., vol. 44, No. 3, 1999, pp. 665-675.

Yan, D., et al., "Adaptive Modification of Treatment Planning to Minimize the Deleterious Effects of Treatment Setup Errors," Int. J. Radiation Oncology Biol. Phys., vol. 37, No. 5, while the publication date is unknown, it is believed to have been published prior to 1999, pp. 1-27.

Yan, D., et al., "Adaptive Radiation Therapy," Phys. Med. Biol., vol. 42, 1997, pp. 123-132.

Yan, D., et al., "An Off-Line Strategy for Constructing a Patient-Specific Planning Target Volume For Image Guided Adaptive Radiotherapy of Prostate Cancer," Int. J. Radiation Oncology Biol. Phys., vol. 48, No. 1, 2000, pp. 289-302.

Yan, D., et al., "The Use of Adaptive Radiation Therapy to Reduce Setup Error: A Prospective Clinical Study," Int. J. Radiation Oncology Biol. Phys., vol. 41, No. 3, 1998, pp. 715-720.

Yan, D., et al., "Strategies for Off-Line and On-Line Image Feedback Adaptive Radiotherapy," Editors: BK Paliwal, DE Herbert, JF Fowler, MP Mehta, Biological & Physical Basis of IMRT & Tomotherapy, AAPM Symposium Proceeding No. 12, 2002, pp. 139-150.

Yan, D., et al., "Computed Tomography Guided Management of Interfractional Patient Variation," Semin. Radiat. Oncol. vol. 15, 2005, pp. 168-179.

Yan, D., et al., "A New Model for "Accept or Reject" Strategies in Off-Line and On-Line Megavoltage Treatment Evaluation", Int. J. Radiat. Oncol. Biol. Phys., 1995, vol. 31, No. 4, pp. 943-952.

Yan, D., et al., "Adaptive Modification of Treatment Planning to Minimize the Deleterious effects of Treatment Setup Errors", Int. J. Radiat. Oncol. Biol. Phys., 1997, vol. 38, No. 1, pp. 197-206.

Yang, Y., et al., "Evaluation of On-Board kV Cone Beam CT (CBCT)-based Dose Calculation," Phys. Med. Biol., vol. 52, 2007, pp. 685-705.

Ying, X.G., et al., "Portal Dose Images. II: Patient Dose Estimation", Int. J. Radiat. Oncol. Biol. Phys., Jun. 1990, vol. 18, No. 6, pp. 1465-1475.

Yu, C.X., et al., "Photon Dose Calculation Incorporating Explicit Electron Transport", Med. Phys., Jul. 1995, vol. 22, No. 7, pp. 1157-1165.

Yu, C.X., et al., "A Method for Implementing Dynamic Photon Beam Intensity Modulation Using Independent Jaws and a Multileaf Collimator", Phys. Med. Biol., 1995, vol. 40, pp. 769-787.

Yu, C.X., et al., "A Multiray Model for Calculating Electron Pencil Beam Distribution", Med. Phys., Sep./Oct. 1988, vol. 15, No. 5, pp. 662-671.

Yu, C.X., et al, "Photon Dose Perturbations Due to Small Inhomogeneities", Med. Phys., Jan./Feb. 1987, vol. 14, No. 1, pp. 78-83.

Zhang, T., et al., "Automatic Delineation of Online Head and Neck CT Images: Towards Online Adaptive Radiotherapy," Int. J. of Radiation Oncology Biol. Phys., vol. 68, No. 2, 2007, pp. 522-530.

Zhang, Tiezhi, et al., "Tetrahedron Beam Computed Tomography (TBCT): A New Design of Volumetric CT System," Phys. Med. Biol., vol. 54, 2009, pp. 3365-3378.

International Search Report and Written Opinion for International Application No. PCT/US2011/000006, mailed Mar. 1, 2011.

International Search Report and Written Opinion for International Application No. PCT/US2007/012607, mailed Apr. 11, 2008, two pages.

Yasuda, Takami "State of the Art and Future Possibility of Image Applications in Medicine"; Institute of Television Engineers of Japan (ITE), vol. 16(47), Jul. 23, 1992, pp. 1-8.

Inamura, Seiya "Future for Digital X-Ray", Montly New Medical Care, vol. 26, No. 4, pp. 72-78, published Apr. 1, 1991 with translation of relevant portions of Abstract.

Japanese Office Action dated Jan. 15, 2015 in JP Application No. 2001-559337.

\* cited by examiner

TETRAHEDRON BEAM COMPUTED TOMOGRAPHY WITH MULTIPLE DETECTORS AND/OR SOURCE ARRAYS

The present application is a continuation-in-part application of U.S. patent application Ser. No. 12/803,480, filed on Jun. 29, 2010 now U.S. Pat. No. 8,611,490, which is a continuation application of U.S. patent application Ser. No. 11/786,781, filed on Apr. 12, 2007, now U.S. Pat. No. 7,760, 849, which claims, under 35 U.S.C. §119(e), the benefit of priority of the filing date of Apr. 14, 2006, of U.S. Provisional Patent Application Ser. No. 60/792,207, filed on the aforementioned date, the entire contents of each of the above mentioned patent and patent applications are incorporated herein by reference.

BACKGROUND OF THE INVENTION

1. Field of the Invention

The present invention relates generally to computed tomography (CT) and, more particularly, to a volumetric computed tomography (VCT) system.

2. Discussion of the Related Art

Computed tomography (CT) provides a transverse image of an object. Conventional fan beam CT uses a point x-ray source and a linear detector array. The detector array may have one or more detector rows. With a single rotation, one or more image slices can be reconstructed using computer algorithms.

In order to increase imaging speed, CT detector row number has been increased to many hundreds so that more image slices are acquired in each rotation. A wider detector array covers a larger field of view. Hence, a volumetric image can be reconstructed with a single gantry rotation. Such CT systems are often called volumetric CT (VCT) systems. VCT systems can use a two-dimensional detector, such as a flat panel imager. VCT systems that include a flat panel imager are commonly used in image guided radiotherapy and intervention as shown in U.S. Pat. No. 6,842,502, the entire contents of which are incorporated herein by reference. The patent describes an embodiment of a cone-beam computed tomography imaging system that includes a kilovoltage x-ray tube and a flat panel imager having an array of amorphous silicon detector. As a patient lies upon a treatment table, the x-ray tube and flat panel image rotate about the patient in unison so as to take a plurality of images as described previously.

FIG. 1 diagrammatically illustrates the geometry of a cone beam computed tomography (CBCT) system. CBCT systems usually include a point x-ray source 20 and a two-dimensional flat panel detector 22 mounted on a gantry. The source 20 and detector 22 rotates together about a central axis 24. The trajectory of source 20 is a full circle 26 or partial arc. X-ray beams generated by the source 20 are attenuated by the imaged subject. The attenuation measured by the detector 22 is used to reconstruct images of the object. With one full or partial rotation, a three-dimensional image of object 28 can be reconstructed using image reconstruction algorithms.

There are several disadvantages when using CBCT. For example, the flat panel detector may include a scintillation screen and a charge-coupled device photodiode array. The scintillation screen converts x-ray photons into visible light photons which are then detected by a photodiode array. The performance of such flat panel detectors, in the aspect of signal-to-noise ratio, detection efficiency and sampling speed, is inferior to discrete x-ray detectors that are used in a diagnostic helical computed tomography scanner. High noise level and low detection efficiency cause poor low contrast differentiation and noisier images. A further reduction in image quality may be caused by suboptimal performance of a flat panel imager. Approximate reconstruction artifacts exist when cone angle is large.

Another disadvantage of CBCT is that when x-ray beams pass through the object 28, x-ray photons are either absorbed or scattered. Since the x-ray detector is so wide, the scattered photons are likely to be detected by the two-dimensional detector 22. Scattered photons will add up on the images, and hence attenuation information cannot be accurately measured. Scatter causes artifacts in the images. CBCT images hence have low image quality than those from fan beam CT. Besides artifacts, scatter contamination also increases noise in the images. In order to compensate noise, stronger x-ray beams have to be used. Hence, x-ray exposure of CBCT imaging is also higher than fan beam CTs. Another problem with such a VCT system is the large cost of a flat panel detector.

Current techniques for scatter correction or rejection include calculating the scatter and then subtracting the scatter from the signal. However, the length of time the scatter calculation requires can be as long as hours or days using the Monte Carlo method. Furthermore, the noise from the scatter remains after the scatter profile has been subtracted from the signal, such that the signal-to-noise ratio decreases.

In another technique, the scatter is measured and then subtracted from the signal. This technique, however, subjects the patient to additional radiation exposure and prolonged scanning time and requires an additional scan to measure the scatter profile. Further, the noise from the scatter remains, which sacrifices the signal-to-noise ratio.

In yet another technique, a grid is positioned in front of the detector and behind the patient to block some scatter. However, the grid also partially blocks the primary x-ray beams, resulting in additional radiation exposure to the patient. Other techniques use an air gap by increasing the distance from the detector to the patient, which reduces the scatter that is collected by the detector. Because of mechanical limitations, however, the distance from the detector to the patient can be increased only a finite amount.

Other systems addressing the scatter problem are known. For example, a VCT system with a two-dimensional x-ray source array and a point or small detector is disclosed in U.S. Pat. No. 7,072,436, the entire contents of which are incorporated herein by reference. This approach is also called inverse geometry CT since the detector and source geometry is reversed. Compared to regular geometry VCT, the scatter component in inverse geometry VCT is very low due to the small detector. However, in practice it is difficult to make a large two-dimensional x-ray source array that can provide sufficient field of view. The two-dimensional x-ray source array is also cumbersome to be used in mobile CT scanners.

Another VCT geometry uses a linear array of x-ray sources, and a two-dimensional area detector as described in U.S. Pat. No. 7,072,436, the entire contents of which are incorporated herein by reference. Each x-ray source generates a fan beam perpendicular to the rotation axis. This system is able to reject scatter photons and perform exact image reconstruction. It also does not have beam divergence problem in the axial direction as cone beam CT.

Note that the use of multiple fan beams in computed tomography as described in U.S. Pat. No. 6,229,870 ("the '870 patent"), the entire contents of which are incorporated herein by reference, does not require expensive area detector. It also uses a linear array of x-ray sources, and the x-ray beam from each source is collimated to its own detector array. The fan beams are also perpendicular to the rotation axis. The gap between the detector arrays can be filled in by moving the imaging subject during gantry rotation. Multiple rotations are needed for generating an image and so the system described in the '870 patent is not a true VCT system.

Tetrahedron beam computed tomography (TBCT) is another VCT system that can reconstruct a three-dimensional volume in a single gantry rotation and is described in U.S. Pat. No. 7,760,849 and U.S. patent application Ser. No. 12/803,480, the entire contents of each of which is incorporated herein by reference. TBCT employs a linear detector array and linear source array which are orthogonal to each other. The linear detector array and linear source array form a tetrahedral volume instead of a cone volume of traditional CBCT. The beams from each individual source of the source array are collimated to fan beams so that scatter component is very low. TBCT does not require a very wide detector so costs are significantly reduced. In addition, a linear array of x-ray sources is relatively easier to make when compared with a two-dimensional source array. The approximate image reconstruction artifact due to cone angle can be eliminated or reduced by using iterative image reconstruction algorithms.

Similar to that of CBCT systems, the beams of TBCT are diverged (converged). In order to achieve certain field of view (FOV) at central axis, the linear source array and detector must be almost twice as long along their respective axes as the desired FOV along those axes. Moreover because of the divergence in axial (z) direction, the volume that received radiation is larger than the volume that can be reconstructed. A mobile CT scanner requires compact design so that it can be easily mounted on C-arm gantries.

Accordingly, it is an object of the present invention to reduce scatter generated in a volumetric computed tomography system.

Another object of the present invention is to provide for a compact volumetric computed tomography system.

Another object of the present invention is to reduce beam divergence in a transverse slice.

Another object of the present invention is to reduce the lengths of detector arrays.

BRIEF SUMMARY OF THE INVENTION

One aspect of the present invention regards a tetrahedron beam computed tomography system including an x-ray source array that sequentially emits a plurality of x ray beams at different positions along a scanning direction and a collimator that intercepts the plurality of x-ray beams so that a plurality of fan-shaped x-ray beams emanate from the collimator towards an object. The system includes a first detector receiving a first set of fan-shaped x ray beams after they pass through the object, the first detector generating a first imaging signal for each of the received first set of fan-shaped x-ray beams and a second detector receiving a second set of fan-shaped x ray beams after they pass through the object, the second detector generating a second imaging signal for each of the received second set of fan-shaped x-ray beams. The system including a computer connected to the first detector and the second detector so as to receive 1) the first imaging signals for each of the first set of received fan-shaped x-ray beams and 2) the second imaging signals for each of the second set of received fan-shaped x-ray beams, wherein the x-ray source array, the first detector and the second detector rotate about a rotation axis so as to rotation about the object so that multiple imaging signals are reconstructed by the computer to generate a three-dimensional tetrahedron beam computed tomography image therefrom. The system further includes a display connected to the computer and displaying the three-dimensional tetrahedron beam computed tomography image.

A second aspect of the present invention regards a method of forming an image of an object, the method including having an x-ray source array, first detector and second detector rotate about an axis of rotation relative to an object and sequentially emitting a plurality of x ray beams from the x-ray source array at different positions along a scanning direction and intercepting the plurality of x-ray beams so that a plurality of fan-shaped x-ray beams emanate towards the object. The method further includes having a first set of fan-shaped x ray beams after they pass through the object received by the first detector, the first detector generating a first imaging signal for each of the received first set of fan-shaped x-ray beams and having a second set of fan-shaped x ray beams after they pass through the object received by the second detector, the second detector generating a second imaging signal for each of the received second set of fan-shaped x-ray beams. The method includes receiving 1) the first imaging signals for each of the first set of received fan-shaped x-ray beams and 2) the second imaging signals for each of the second set of received fan-shaped x-ray beams, wherein rotation of the x-ray source array, the first detector and the second detector rotate about the axis of rotation results in multiple imaging signals being reconstructed to generate a three-dimensional tetrahedron beam computed tomography image therefrom. The method further including displaying the three-dimensional tetrahedron beam computed tomography image.

A third aspect of the present invention regards a tetrahedron beam computed tomography system that includes a first x ray source array that sequentially emits a first plurality of x ray beams at different positions along a first scanning direction and a first collimator that intercepts the first plurality of x-ray beams so that fan-shaped x-ray beams emanate from the first collimator towards an object. The system further includes a second x ray source array that sequentially emits a second plurality of x ray beams at different positions along a second scanning direction and a second collimator that intercepts the second plurality of x-ray beams so that fan-shaped x-ray beams emanate from the second collimator towards the object. The system includes a first detector receiving one or both of 1) a first plurality of fan-shaped x ray beams from the first x-ray source array and 2) a first plurality of fan-shaped x-ray beams from the second x-ray source array after they pass through the object, the first detector generating a first imaging signal for each of the received one or both of the first plurality of fan-shaped x-ray beams from the first x-ray source array and the first plurality of fan-shaped x-ray beams from the second x-ray source array. The system also includes a second detector receiving one or both of 1) a second plurality of fan-shaped x ray beams from the first x-ray source array and 2) a second plurality of fan-shaped x-ray beams from the second x-ray source array after they pass through the object, the second detector generating a second imaging signal for each of the received one or both of the second plurality of fan-shaped x-ray beams from the first x-ray source array and the second plurality of fan-shaped x-ray beams from the second x-ray source array. The system further includes a computer connected to the first detector and the second detector so as to receive 1) the first imaging signals for each of the first plurality of fan-shaped x-ray beams received by the first detector and 2) the second imaging signals for each of the second plurality of fan-shaped x-ray beams received by the second detector, wherein the first x-ray source array, the second x-ray source array, the first detector and the second detector rotate about a rotation axis so as to rotation about the object so that multiple imaging signals are reconstructed by the computer to generate a three-dimensional tetrahedron beam computed tomography image therefrom. The system including a display connected to the computer and displaying said three-dimensional tetrahedron beam computed tomography image.

A fourth aspect of the present invention regards a method of forming an image of an object, the method including having a first x ray source array, a second x-ray source array, a first detector and a second detector rotate about an axis of rotation relative to an object. The method including 1) sequentially emitting a first plurality of x ray beams from the first x-ray source array at different positions along a first scanning direction and intercepting the first plurality of x-ray beams and 2) sequentially emitting a second plurality of x ray beams from the second x-ray source array at different positions along a second scanning direction and intercepting the second plurality of x-ray beams so that a plurality of fan-shaped x-ray beams emanate towards the object. The method including having the first detector receive one or both of 1) a first plurality of fan-shaped x-ray beams from the first x-ray source array and after they pass through the object and 2) a first plurality of fan-shaped x-ray beams from the second x-ray source array and after they pass through the object, wherein the first detector generates a first imaging signal for each of the received first plurality of fan-shaped x-ray beams from the first x-ray source array and the received first plurality of fan-shaped x-ray beams from the second x-ray source array. The method including having the second detector receive one or both of 1) a second plurality of fan-shaped x-ray beams from the first x-ray source array and after they pass through the object and 2) a second plurality of fan-shaped x-ray beams from the second x-ray source array and after they pass through the object, wherein the second detector generates a second imaging signal for each of the received second plurality of fan-shaped x-ray beams from the first x-ray source array and the received second plurality of fan-shaped x-ray beams received from the second x-ray source array. The method including receiving 1) the first imaging signals for each of the first plurality of fan-shaped x-rays from the first x-ray source array and for each of the first plurality of fan-shaped x-ray beams from the second x-ray source array and 2) the second imaging signals for each of the second plurality of fan-shaped x-ray beams from the first x-ray source array and for each of the second plurality of fan-shaped x-ray beams from the second x-ray source array, wherein rotation of the first x-ray source array, the second x-ray source array, the first detector and the second detector about the axis of rotation results in multiple imaging signals being reconstructed to generate a three-dimensional tetrahedron beam computed tomography image therefrom. The method including displaying the three-dimensional tetrahedron beam computed tomography image.

One or more aspects of the present invention provide the advantage of providing a compact volumetric CT system capable of rejecting the majority of scatter photons.

One or more aspects of the present invention provide the advantage of reducing or eliminating beam divergence so that the field of view can be increased.

One or more aspects of the present invention provide the advantage of reducing the lengths of source array.

One or more aspects of the present invention provide the advantage of reducing the lengths of detector arrays.

Additional objects, advantages and features of the present invention will become apparent from the following description and the appended claims when taken in conjunction with the accompanying drawings.

BRIEF DESCRIPTION OF THE DRAWINGS

FIG. 3b schematically shows a front cross-sectional view of the x-ray source array of FIG. 3a;

PREFERRED EMBODIMENTS OF THE INVENTION

Figure 1:
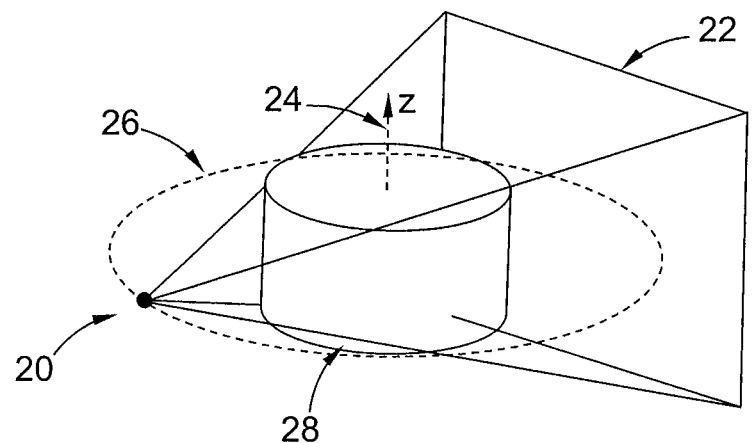
FIG. 1 schematically depicts a known cone-beam computed tomography system.
Figure 2:
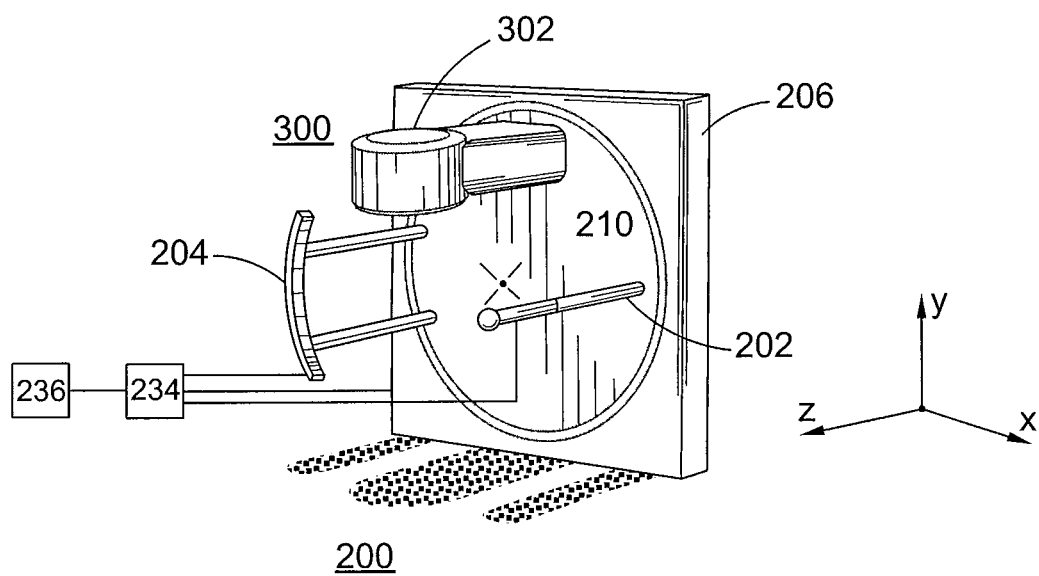
FIG. 2 schematically shows an embodiment of a tetrahedron beam computed tomography system used in conjunction with a radiotherapy source in accordance with the present invention.

Referring now to FIGS. 2-12, various imaging systems embodying the principles of the present invention are illustrated, wherein like elements are denoted by like numerals. In particular, FIG. 2 shows an embodiment of a wall-mounted tetrahedron beam computed tomography system 200 and megavoltage portal imaging system 300. The system 200 may be retrofitted onto an existing or new radiation therapy system that includes a separate radiation therapy x-ray source. As shown in FIG. 2, the system 200 includes a separate radiation therapy x-ray source, such as a linear accelerator 302, which is separately mounted to the rotating drum 210. The linear accelerator 302 operates at a power level higher than that of x-ray source 202 so as to allow for treatment of a target volume in a patient lying on movable table (not shown). The table is movable in the x, y and z-directions shown in FIG. 2 via computer 234. The linear accelerator 302 generates a beam of x-rays or particles, such as photons or electrons, which have an energy ranging from 4 MeV to 25 MeV.

The tetrahedron beam computed tomography system 200 includes an x-ray source array 202 and a multi-row imager/detector 204 having a curved shape mounted on a gantry 206. In particular, x-ray source array 202 is preferably a linear array of x-ray source and the multi-row detector is preferably a discrete scintillator/photodiode detector array. The detector array can be constructed from photodiode/scintillator array modules with data acquisition units, which are well known in the art.

As shown in FIG. 2, the detector 204 can be mounted to the face of a flat, circular, rotatable drum 210 of the gantry 206 of a medical linear accelerator 302. Note that in the situation where the x-ray source 202 and detector array 204 are mounted on rotating drum 210, they are arranged to be aligned perpendicular to (source 202) and within (array 204) the rotation plane defined by the drum 210. Note that an example of mounting of an x-ray source and an imager to a rotatable drum is described in U.S. Pat. No. 6,842,502, the entire contents of which are incorporated herein by reference.

Figure 3A:
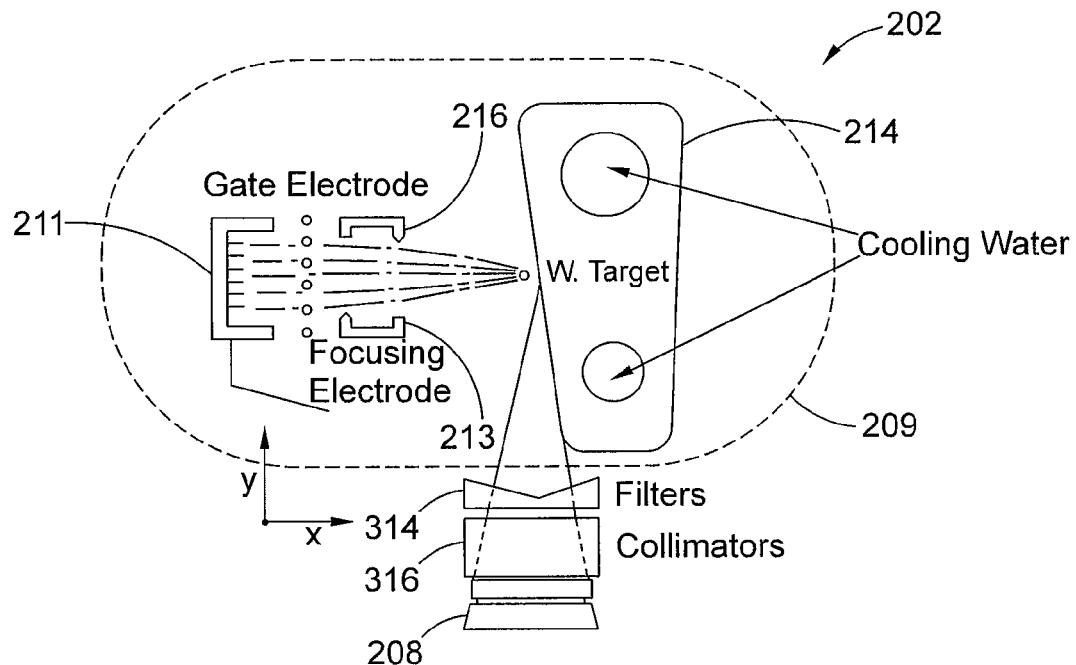
FIG. 3a schematically shows a side cross-sectional view of an embodiment of an x-ray source array to be used with the tetrahedron beam computed tomography system of FIG. 6 in accordance with the present invention.
Figure 3B:
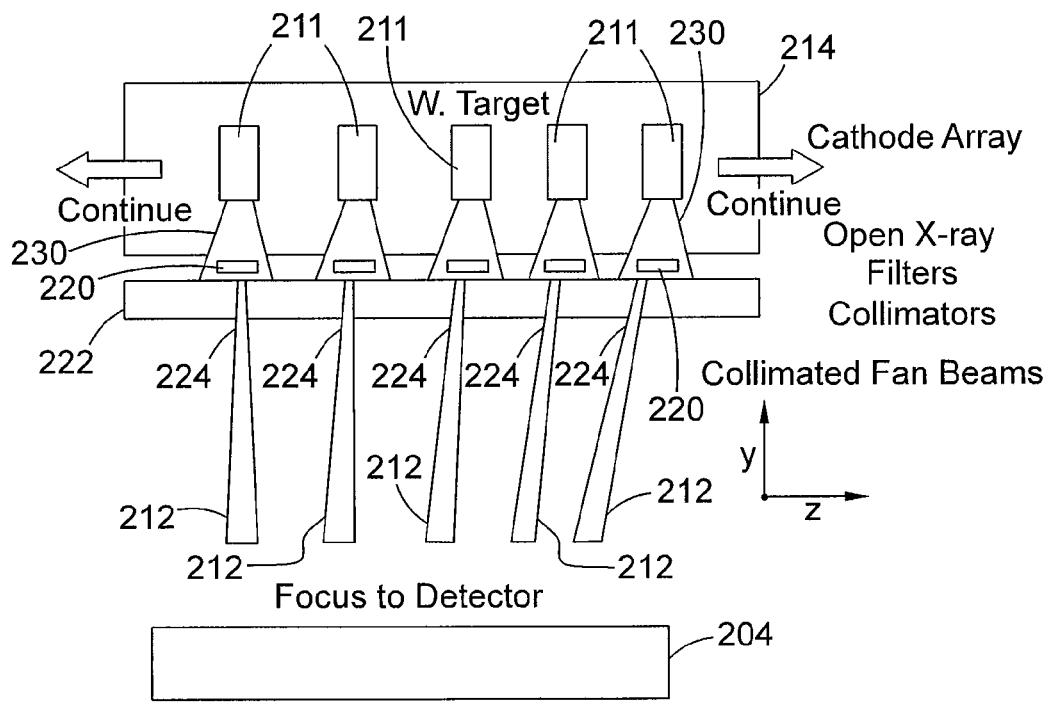
Figure 4A:
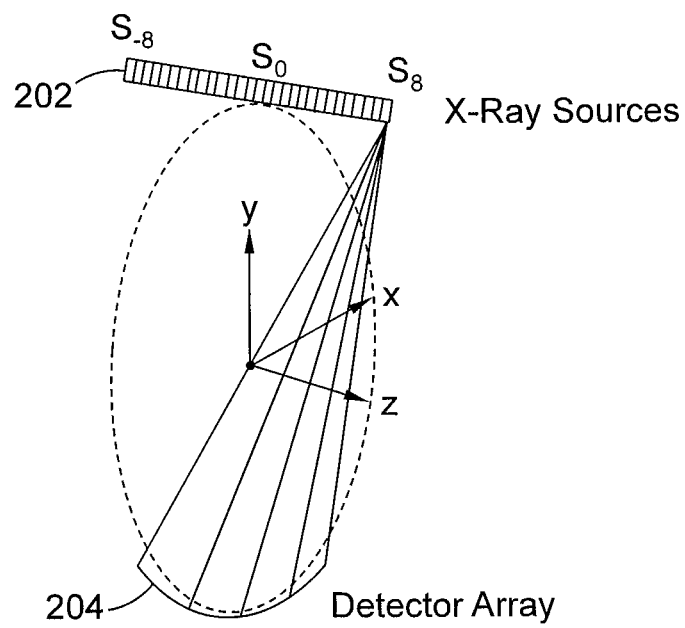
FIGS. 4a-b schematically show a configuration using a linear x-ray source array and curved slot collimator with the systems of FIGS. 2-3b.
Figure 4B:
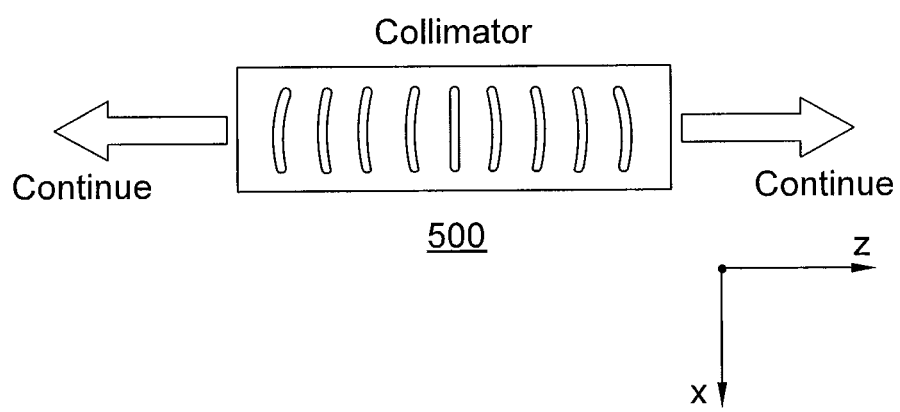

As shown in FIGS. 3a-b, the x-ray source array 202 includes a single, cylindrical-like glass tube 209 within a vacuum pressure. Other possible materials for the tube are copper and aluminum. A plurality of cathodes, such as thermionic cathodes 211, are equally spaced from one another.

In operation, electrons are generated from the cathode 211 by the potential $V_g$ applied between the gate electrode 213 and the cathode 211. The electrons are accelerated by potential $V_a$, and focused into a small focus spot by potential $V_f$ and focusing electrodes 216. X-ray photons are generated via the bremsstrahlung effect when electrons strike on the molybdenum or tungsten anode target 214 and have an energy of about 80-130 keV when imaging a human. The focusing electrodes 216 direct the electrons to different portions of the anode target 214 that represent focus spots that generate individual x-ray beams. Note that in another embodiment, an x-ray source array 202 can be formed by scanning a single electron beam emitted from a single cathode.

As shown in FIGS. 3a-b, the x-ray source array 202 includes a single anode 214 and a plurality of the cathodes 211, wherein each cathode 211 or gate is controlled by a controller, such as MOSFET switches (not shown).

As described in U.S. Pat. No. 7,760,849, x-ray sources are sequentially switched on and off at a rate of approximately a few hundred Hz during a scan. As shown in FIG. 3b, the electrons emanating from each cathode 211 strike a different portion of the anode 214 and so a plurality of x-ray beams 230 are formed sequentially at different positions along the z-axis. The x-ray beams 230 pass through corresponding filters 220 and a stationary (relative to the x-ray source 801) collimator 222. The collimator 222 defines slots 224 which correspond to the cathodes 211. The slots 224 can be rectangular in shape with a width less than that of the beams 230 so that fan beams 212 are formed and which are directed to detector 204, as shown in FIGS. 2 and 3b. With the sequential switching on and off of the source, a fan shaped beam sweeps across the patient or object to be imaged. During this process, the gantry 210 slowly rotates around the patient so that a plurality of two-dimensional images are captured that can be used to generate a three-dimensional tetrahedron beam computed tomography image.

The embodiments described above can be implemented in various cone (wide) beam computed tomography systems, including on-board cone-beam computed tomography radiotherapy units, multi-row detector helical computed tomography systems, multi-row detector axial computed tomography systems, and C-arm flat panel cone-beam computed tomography systems, as well as other conventional diagnostic computed tomography systems. The applications of tetrahedron beam computed tomography can be employed in other forms of image guided interventions, such as image-guided surgery/biopsy with C-arm cone-beam computed tomography. The scatter rejection mechanism of tetrahedron beam computed tomography is also applicable to multi-row helical scanners and digital tomosynthesis.

Figure 5:
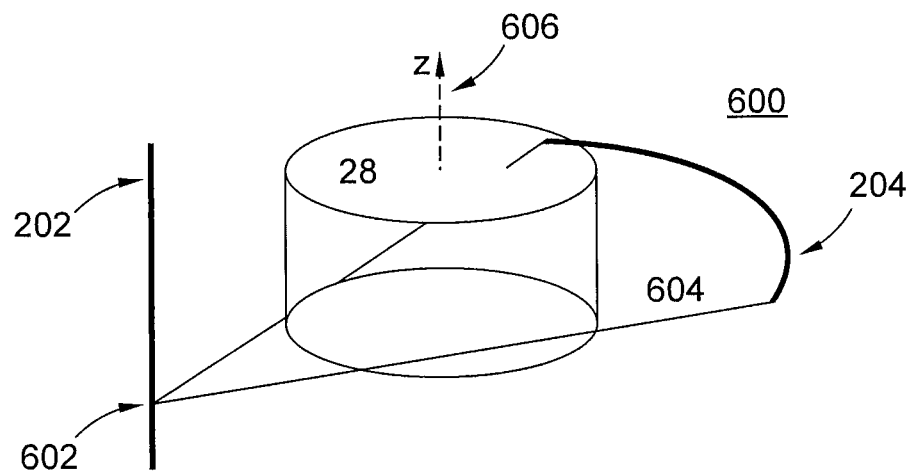
FIG. 5 schematically shows an embodiment of a tetrahedron beam computed tomography system.
Figure 6:
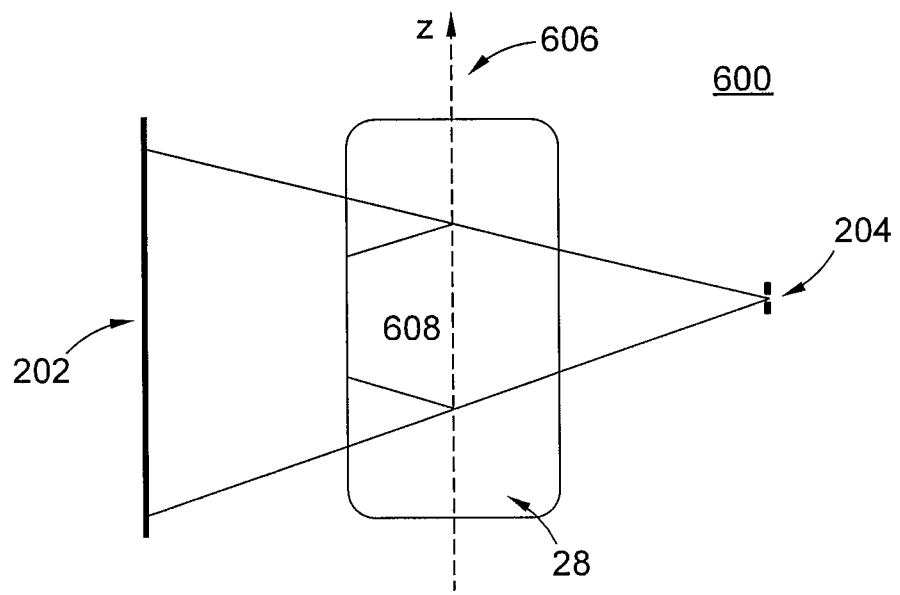
FIG. 6 schematically shows a cross-sectional view of the tetrahedron computed tomography system of FIG. 5.

A tetrahedron beam computed tomography system 600 that employs the components described previously with respect to FIGS. 2, 3a-b and 4a-b is schematically shown in FIGS. 5 and 6. In particular, FIG. 2 illustrates the geometry of tetrahedron beam computed tomography system 600. The system 600 includes an array of x-ray sources 202 and an array of x-ray detectors 204, 230 that rotate about an axis 606. Such rotation can be accomplished by having the x-ray sources and x-ray detectors mounted on a rotating drum 210 of gantry 206.

The source array 202 and detector array 204, 230 are orthogonal to each other. Both source array and detector array can be straight or curved. Each individual source 602 generates an x-ray beam which is collimated to a fan-shaped beam 604 by a multi-slot collimator 222 (not shown). The array of sources 202 generates fan beams at different angles which are received by the same detector 204, 230. Similar to cone-beam computed tomography, a volumetric image can be reconstructed by tetrahedron beam computed tomography with a single rotation. But different from cone-beam computed tomography, the detector array 204, 230 of tetrahedron beam computed tomography receives much less scatter photons due to the fan beam geometry. Consequently, tetrahedron beam computed tomography image quality and imaging dose are significantly improved.

Now referring to FIG. 6, after a rotation about axis 606, both tetrahedron beam computed tomography and cone beam computed tomography are able to reconstruct the shaded volume 608. Due to the beam divergence, the source array needs to be about twice as large as the shaded area. For example, in order to achieve 20 cm field of view in z dimension, the source array 202 needs to be about 40 cm long. Longer source array is more expensive to build and less convenient to mount on gantry. Besides longer tube, the other problem of beam divergence is that the actual volume irradiated is larger than the volume 608. Some region of imaged subject 28 receives radiation but cannot be imaged.

Figure 7:
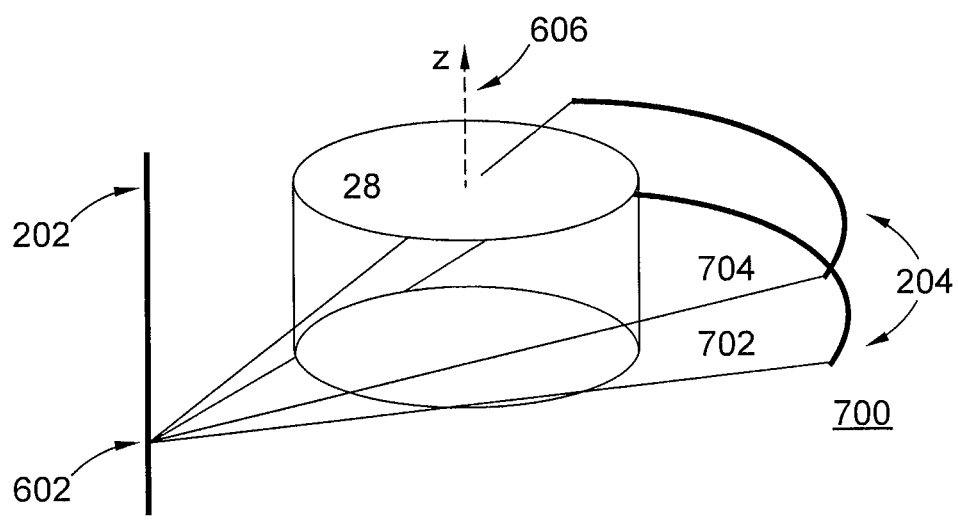
FIG. 7 schematically shows another embodiment of a tetrahedron beam computed tomography system in accordance with the present invention.
Figure 8:
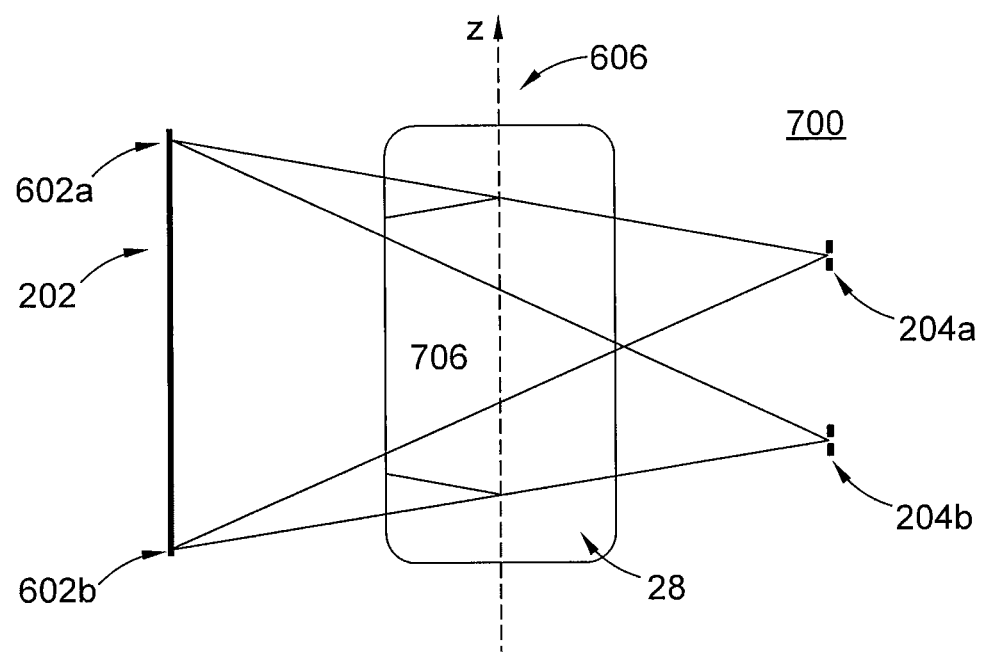
FIG. 8 schematically shows a cross-sectional view of the tetrahedron computed tomography system of FIG. 7.

FIG. 7 shows a tetrahedron beam computed tomography system 700 with two detector arrays 204a and 204b. The two detector arrays 204a and 204b are offset from the central plane that bisects source array 202 and is perpendicular to axis 606. Each x-ray individual source 602 of source array 202 forms two fan beams 702 and 704 which are received by the two detector arrays 204a and 204b, respectively. The fan beams can be received by one of or both of detector arrays 204a and 204b. Or different x-ray beams may be collimated to one of the two detector array, alternatively. The source array 202 forms a tetrahedral volume with each of the detector arrays 204a and 204b. FIG. 8 is a lateral view of the tetrahedron beam computed tomography system 700, wherein sources 602a and 602b are the two outermost sources on the source array 202. As shown in FIG. 8, the reconstructed volume 706 of tetrahedron beam computed tomography system 700 is much wider than the volume 608 of the tetrahedron beam computed tomography system 600 of FIG. 6. There may be still divergence but the angle is much smaller than that shown in FIG. 6. Note that source array 202 is preferably a linear multi-beam x-ray source and each detector array 204a and 204b is preferably a discrete scintillator/photodiode detector array. The detector array can be constructed from photodiode/scintillator array modules with data acquisition units, which are well known in the art.

Figure 9:
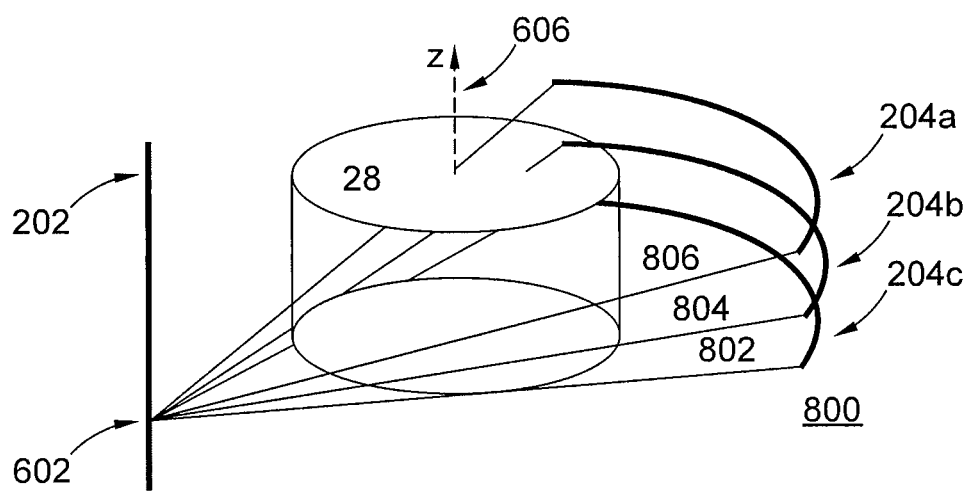
FIG. 9 schematically shows another embodiment of a tetrahedron beam computed tomography system in accordance with the present invention.
Figure 10:
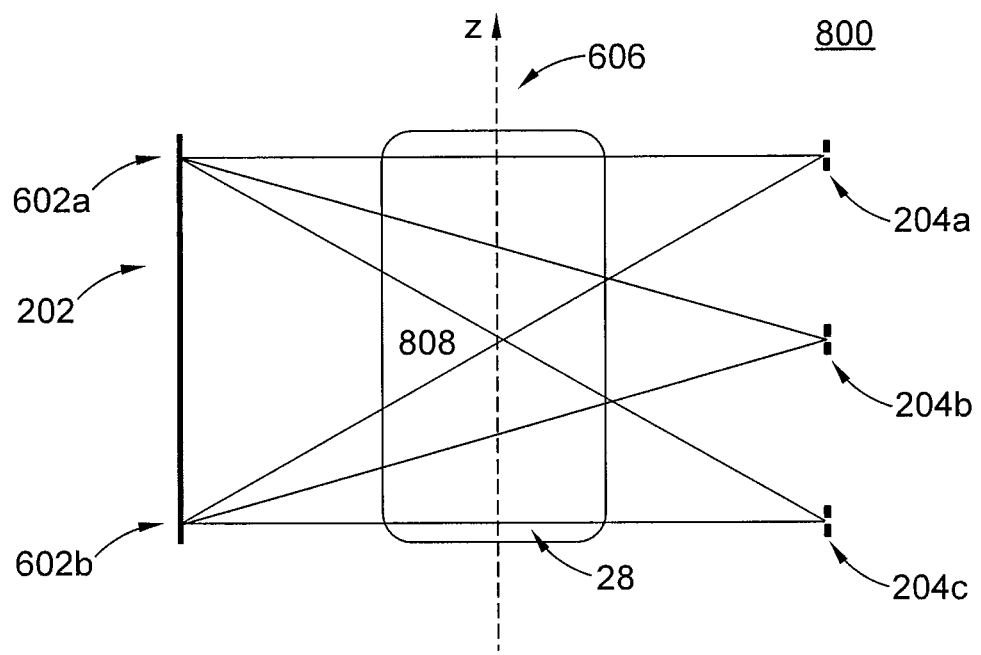
FIG. 10 schematically shows a cross-sectional view of the tetrahedron computed tomography system of FIG. 9.

Similarly three detector arrays can further reduce or eliminate the beam divergence. FIG. 9 shows a tetrahedron beam computed tomography system 800 with three detector arrays. One detector array 204b is located in the central plane and the other detector arrays 204a and 204c are offset from the central plane that bisects source array 202 and is perpendicular to axis 606. The source array 202 generates three fan beams 806, 804 and 802 that pass through the object 28 and are received by detector arrays 204a, 204b and 204c, respectively. The fan beams can be received by one of, two of or all three of detector arrays 204a, 204b and 204c. The source array 202 forms one tetrahedral volume with each detector array. As shown in FIG. 10, the divergence of the x-ray beams can be totally eliminated in this configuration. In particular, the volume 808 that can be reconstructed is the same as the length of the x-ray source array 202. Hence a much shorter x-ray source array is needed. For example, a 20 cm long source array can reconstruct 20 cm field of view in the axial (z) dimension.

Note that in the systems 700 and 800 of FIGS. 7-10, the curved detector arrays have a radius of curvature that is centered about the longitudinal axis of the source array 202. With multiple detector arrays, the beam divergence in z direction is greatly reduced. The source array 202 is equal or slightly larger than the field of view in z direction. However, the beam divergence in the transverse plane remains the same. The lengths of detector arrays 204 are about double the field of view in the transverse plane. For example if a 50 cm field of view is needed in the transverse plane, the detector length would be 80-100 cm depending on the ratio of the source-axis to detector-axis distance.

As described above, the systems 700 and 800 operate by having the source and detector arrays rotate about the axis 606 and acquiring and processing image data in a manner similar to that described in U.S. Pat. No. 7,760,849. Reconstruction of the image data can be done by using a CT reconstruction algorithm or a digital tomosynthesis algorithm in a well known manner The systems 700 and 800 can achieve rotation of the x-ray sources and x-ray detectors by having them mounted on a rotating drum 210 of gantry 206 of FIG. 2 or implemented on a C-arm gantry, robotic arm gantry or closed ring gantry, movable C-arm of a stationary or mobile x-ray imaging device. Note that axial scans of the object (object stationary) or helical scans of the object (object moves to generate helical scan) can be performed. In addition, full, multiple and partial rotations of the sources and detectors can be performed. The three-dimensional data is shown on a display, not shown.

Figure 11:
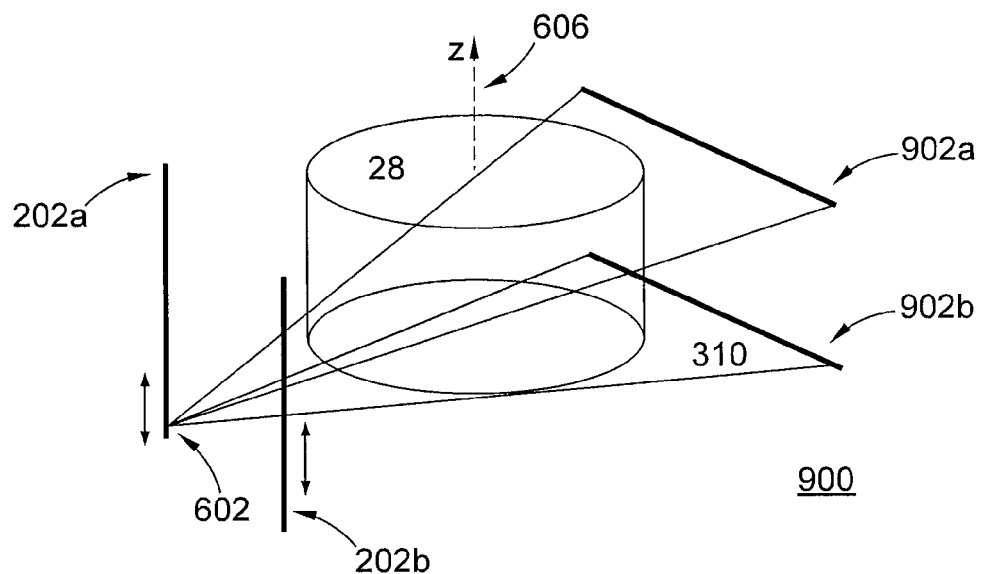
FIG. 11 schematically shows another embodiment of a tetrahedron beam computed tomography system in accordance with the present invention.

In an alternative embodiment, multiple source arrays 202a and 202b can be used in a tetrahedron beam computed tomography system 900 as shown in FIG. 11. The source arrays are parallel to the central axis 606, but positioned a distance offset from the central axis 606. Using multiple source arrays can reduce beam divergence in the transverse plane. With reduced divergence, shorter detector arrays can be used to achieve the same field of view in a transverse plane. In addition, the use of multiple detector arrays 902a and 902b offset from the central plane can allow for the use of shorter source arrays and the reduction of beam divergence in the axial direction. At least two source arrays are offset from the center so that the divergence in transverse plane is also reduced.

Figure 12:
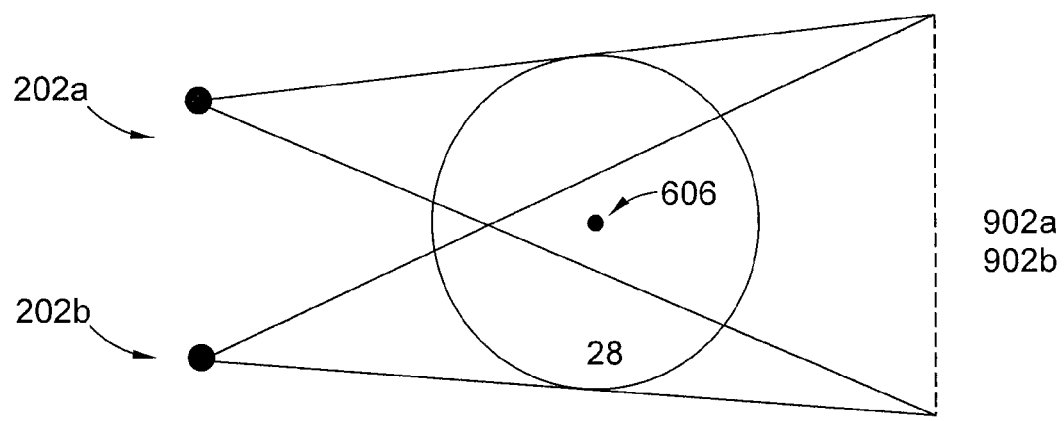
FIG. 12 schematically shows a cross-sectional view of the tetrahedron computed tomography system of FIG. 11.

As shown in FIG. 12, the two source arrays 202a and 202b are offset from the central axis 606. The divergence of the beams is smaller. Hence much shorter detector arrays 202a and 202b can cover the field of view of object 28. Because the detector arrays 902a and 902b are so short, it is unnecessary to use curved detectors. Both detector arrays 902a and 902b and source arrays 202a and 202b can be straight.

One advantage of TBCT system 900 is increased field of view. For example, in order to achieve the same field of view, the length of linear source array and detector array can be reduced by half. Another advantage of system 900 is that only the volume that can be reconstructed will be irradiated. With shorter sources and detectors, the TBCT system can be much more compact and suitable for use as mobile CT scanners.

The system 900 also produces diagnostic quality images due to scatter rejection and the use of high quality detectors.

Note that in the system 900 of FIGS. 11 and 12, the detector arrays are spaced apart from one another by a certain distance and the sources are spaced apart from one another by a certain distance, wherein the distances depend on the particular geometry being used. In addition, the concept of system 900 can be expanded to include sources and detectors that surpass two in number.

Note in the system 800 and 900, the beam from each source is unnecessary to be collimated to all detectors. They can be collimated to one or two detector arrays. With an increase in the field of view in the z-direction, the number of detector arrays may surpass three.

Note that in each of the tetrahedron beam computed tomography systems illustrated in FIGS. 2-12, the detector array forms a tetrahedron volume with the linear source array. Usually the requirement of field of view in z direction is much larger than field of view in transverse plane. For example, regular CT images may have 20 cm length in z direction and 50 cm field of view in transverse plane. In systems 700, 800 and 900, it is preferable to have source array(s) perpendicular to rotation plane and detector arrays parallel to rotation planes. This is because it is easier to make a long detector array than a long source array.

With the use of multiple source arrays in system 900, the length of the source arrays and detector arrays may be similar. In this case, it does not matter which one of the detector and source is parallel to the rotation axis. Hence the positions of source arrays and detector arrays shown in FIGS. 2-16 can be switched. In addition, the fan beams can be received by one of or both of detector arrays 902a and 902b.

As described above, the system 900 operates by having the source and detector arrays rotate about the axis 606 and acquiring and processing image data in a well known manner. Reconstruction of the image data can be done by using a CT reconstruction algorithm or a digital tomosynthesis algorithm, wherein the latter has a lower image quality and is used when smaller angles of rotation of the sources and detectors are involved. Such rotation can be accomplished by having the x-ray sources and x-ray detectors mounted on a rotating drum 210 of gantry 206 of the radiation treatment machine of FIG. 2 or implemented on a C-arm gantry, robotic arm gantry or closed ring gantry. Note that axial scans of the object (object stationary) or helical scans of the object (object moves to generate helical scan) can be performed. In addition, full, multiple and partial rotations of the sources and detectors can be performed. The three-dimensional data is shown on a display, not shown.

The systems 700, 800 and 900 can have full rotation with the gantry or partial rotation. The rotation can be axial or helical depending on the image reconstruction algorithms. The data acquired by the system can be used for 3D CT image reconstruction or digital tomosynthesis image reconstruction.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims. For example, the number of source array can be more than two. Each of the detectors does not have to receive x-ray fan beams from all sources.

We claim:

1. A tetrahedron beam computed tomography system comprising:
    an x-ray source array that sequentially emits a plurality of x-ray beams at different positions along a scanning direction;
    a collimator that intercepts said plurality of x-ray beams so that a plurality of fan-shaped x-ray beams emanate from said collimator towards an object;
    a first detector receiving a first set of fan-shaped x-ray beams after they pass through said object, said first detector generating a first imaging signal for each of said received first set of fan-shaped x-ray beams;
    a second detector receiving a second set of fan-shaped x-ray beams after they pass through said object, said second detector generating a second imaging signal for each of said received second set of fan-shaped x-ray beams;
    a computer connected to said first detector and said second detector so as to receive 1) said first imaging signals for each of said first set of received fan-shaped x-ray beams and 2) said second imaging signals for each of said second set of received fan-shaped x-ray beams, wherein said x-ray source array, said first detector and said second detector rotate about a rotation axis so as to rotate about said object so that multiple imaging signals are reconstructed by said computer to generate a three-dimensional tetrahedron beam computed tomography image therefrom; and
    a display connected to said computer and displaying said three-dimensional tetrahedron beam computed tomography image.

2. The tetrahedron beam computed tomography system of claim 1, wherein said x-ray source array comprises a linear array of kV x-ray sources.

3. The tetrahedron beam computed tomography system of claim 1, wherein said collimator comprising a plurality of slots, wherein each of said plurality of said slots corresponds to one of said different positions.

4. The tetrahedron beam cone beam computed tomography system of claim 3, wherein said collimator is stationary with respect to said x-ray source array.

5. The tetrahedron beam cone beam computed tomography system of claim 1, wherein said x-ray source array comprise a plurality of discrete sources of x-rays or focus spots.

6. The tetrahedron beam computed tomography system of claim 1, wherein said first detector is a two-dimensional array of individual detector elements.

7. The tetrahedron beam computed tomography system of claim 1, wherein said first detector is a one-dimensional array of individual detector elements.

8. The tetrahedron beam computed tomography system of claim 1, wherein said first detector is straight and said second detector is straight.

9. The tetrahedron beam computed tomography system of claim 1, wherein said first detector is curved and said second detector is curved.

10. The tetrahedron beam computed tomography system of claim 1, wherein said x-ray source array is linear, wherein a longitudinal axis of the x-ray source array is parallel to said rotation axis.

11. The tetrahedron beam computed tomography system of claim 10, wherein said first detector is offset from a central plane that bisects said x-ray source array and is perpendicular to said rotation axis.

12. The tetrahedron beam computed tomography system of claim 11, wherein said second detector is offset from said central plane.

13. The tetrahedron beam computed tomography system of claim 12, wherein said first detector is straight and said second detector is straight.

14. The tetrahedron beam computed tomography system of claim 12, wherein said first detector is curved and said second detector is curved.

15. The tetrahedron beam computed tomography system of claim 1, further comprising a third detector receiving a third set of fan-shaped x-ray beams after they pass through said object, said third detector generating a third imaging signal for each of said received third set of fan-shaped x-ray beams, wherein said computer is connected to said third detector so as to receive said third imaging signals for each of said third set of received fan-shaped x-ray beams, wherein said third detector rotates about said rotation axis so as to rotate about said object so that multiple imaging signals are reconstructed by said computer to generate said three-dimensional tetrahedron beam computed tomography image therefrom.

16. The tetrahedron beam computed tomography system of claim 12, further comprising a third detector receiving a third set of fan-shaped x-ray beams after they pass through said object, said third detector generating a third imaging signal for each of said received third set of fan-shaped x-ray beams, wherein said computer is connected to said third detector so as to receive said third imaging signals for each of said third set of received fan-shaped x-ray beams, wherein said third detector rotates about said rotation axis so as to rotate about said object so that multiple imaging signals are reconstructed by said computer to generate said three-dimensional tetrahedron beam computed tomography image therefrom.

17. The tetrahedron beam computed tomography system of claim 16, wherein said third detector is intersected by said central plane.

18. The tetrahedron beam computed tomography system of claim 17, wherein said third detector lies between said first detector and said second detector.

19. The tetrahedron beam computed tomography system of claim 1, wherein said x-ray source array, said first detector and said second detector are mounted on a rotation gantry.

20. The tetrahedron beam computed tomography system of claim 19, wherein said rotation gantry rotates a full, partial rotation or multiple rotation during a scan of said object by said x-ray source array.

21. The tetrahedron beam computed tomography system of claim 1, wherein said x-ray source array performs an axial scan of said object.

22. The tetrahedron beam computed tomography system of claim 1, wherein said x-ray source array performs a helical scan of said object.

23. The tetrahedron beam computed tomography system of claim 1, wherein said computer reconstructs said first and second imaging signals using a CT reconstruction algorithm.

24. The tetrahedron beam computed tomography system of claim 1, wherein said computer reconstructs said first and second imaging signals using a digital tomosynthesis algorithm.

25. A method of forming an image of an object, the method comprising:
    having an x-ray source array, first detector and second detector rotate about an axis of rotation relative to an object;
    sequentially emitting a plurality of x ray beams from said x-ray source array at different positions along a scanning direction;

intercepting said plurality of x-ray beams so that a plurality of fan-shaped x-ray beams emanate towards said object;

having a first set of fan-shaped x ray beams after they pass through said object received by said first detector, said first detector generating a first imaging signal for each of said received first set of fan-shaped x-ray beams;

having a second set of fan-shaped x ray beams after they pass through said object received by said second detector, said second detector generating a second imaging signal for each of said received second set of fan-shaped x-ray beams;

receiving 1) said first imaging signals for each of said first set of received fan-shaped x-ray beams and 2) said second imaging signals for each of said second set of received fan-shaped x-ray beams, wherein rotation of said x-ray source array, said first detector and said second detector about said axis of rotation results in multiple imaging signals being reconstructed to generate a three-dimensional tetrahedron beam computed tomography image therefrom; and displaying said three-dimensional tetrahedron beam computed tomography image.

26. The method of claim 25, wherein said x-ray source array comprises a linear array of kV x-ray sources.

27. The method of claim 25, wherein said first detector is straight and said second detector is straight.

28. The method of claim 25, wherein said first detector is curved and said second detector is curved.

29. The method of claim 25, wherein said x-ray source array is linear, wherein a longitudinal axis of the x-ray source array is parallel to said rotation axis.

30. The method of claim 29, wherein said first detector is offset from a central plane that bisects said x-ray source array and is perpendicular to said rotation axis.

31. The method of claim 30, wherein said second detector is offset from said central plane.

32. The method of claim 31, wherein said first detector is straight and said second detector is straight.

33. The method of claim 31, wherein said first detector is curved and said second detector is curved.

34. The method of claim 25, further comprising having a third set of fan-shaped x ray beams after they pass through said object received by a third detector, said third detector generating a third imaging signal for each of said received third set of fan-shaped x-ray beams, wherein said third imaging signal is reconstructed to generate said three-dimensional tetrahedron beam computed tomography image therefrom.

35. The method of claim 25, wherein said x-ray source array, said first detector and said second detector are mounted on a rotation gantry.

36. The method of claim 35, wherein said rotation gantry rotates a full, partial rotation or multiple rotation during a scan of said object by said x-ray source array.

37. The method of claim 25, wherein said x-ray source array performs an axial scan of said object, wherein said object is stationary.

38. The method of claim 25, wherein said x-ray source array performs a helical scan of said object, wherein said helical scan is in part due to said object moving during said scan.

39. The method of claim 25, wherein said reconstructing of said multiple imaging signals is performed by using a CT reconstruction algorithm.

40. The method of claim 25, wherein said reconstructing of said multiple imaging signals is performed by using a digital tomosynthesis algorithm.

41. A tetrahedron beam computed tomography system comprising:

a first x-ray source array that sequentially emits a first plurality of x-ray beams at different positions along a first scanning direction;

a first collimator that intercepts said first plurality of x-ray beams so that fan-shaped x-ray beams emanate from said first collimator towards an object;

a second x-ray source array that sequentially emits a second plurality of x-ray beams at different positions along a second scanning direction;

a second collimator that intercepts said second plurality of x-ray beams so that fan-shaped x-ray beams emanate from said second collimator towards said object;

a first detector receiving one or both of 1) a first plurality of fan-shaped x-ray beams from said first x-ray source array and 2) a first plurality of fan-shaped x-ray beams from said second x-ray source array after they pass through said object, said first detector generating a first imaging signal for each of said received one or both of said first plurality of fan-shaped x-ray beams from said first x-ray source array and said first plurality of fan-shaped x-ray beams from said second x-ray source array;

a second detector receiving one or both of 1) a second plurality of fan-shaped x-ray beams from said first x-ray source array and 2) a second plurality of fan-shaped x-ray beams from said second x-ray source array after they pass through said object, said second detector generating a second imaging signal for each of said received one or both of said second plurality of fan-shaped x-ray beams from said first x-ray source array and said second plurality of fan-shaped x-ray beams from said second x-ray source array;

a computer connected to said first detector and said second detector so as to receive 1) said first imaging signals for each of said first plurality of fan-shaped x-ray beams received by said first detector and 2) said second imaging signals for each of said second plurality of fan-shaped x-ray beams received by said second detector, wherein said first x-ray source array, said second x-ray source array, said first detector and said second detector rotate about a rotation axis so as to rotate about said object so that multiple imaging signals are reconstructed by said computer to generate a three-dimensional tetrahedron beam computed tomography image therefrom; and a display connected to said computer and displaying said three-dimensional tetrahedron beam computed tomography image.

42. The tetrahedron beam computed tomography system of claim 41, wherein said x-ray source array comprises a linear array of kV x-ray sources.

43. The tetrahedron beam computed tomography system of claim 41, wherein said first x-ray source array is linear that extends along a longitudinal direction and said second x-ray source array is linear and is parallel to said first x-ray source array.

44. The tetrahedron beam computed tomography system of claim 43, wherein said first detector is linear and said second detector is linear and is parallel to said first detector and is perpendicular to said longitudinal direction.

45. The tetrahedron beam computed tomography system of claim 44, wherein said longitudinal direction is parallel to said axis of rotation.

46. The tetrahedron beam computed tomography system of claim 44, wherein said longitudinal direction is perpendicular said axis of rotation.

47. The tetrahedron beam computed tomography system of claim 41, wherein said first detector is offset from a central plane that bisects said first x-ray source array and is perpendicular to said rotation axis.

48. The tetrahedron beam computed tomography system of claim 47, wherein said second detector is offset from said central plane.

49. The tetrahedron beam computed tomography system of claim 41, wherein said first x-ray source array, said second x-ray source array, said first detector and said second detector are mounted on a rotation gantry.

50. The tetrahedron beam computed tomography system of claim 49, wherein said rotation gantry rotates a full, partial rotation or multiple rotation during a scan of said object by said first x-ray source array and said second x-ray source array.

51. The tetrahedron beam computed tomography system of claim 41, wherein said first x-ray source array and second x-ray source array perform an axial scan of said object.

52. The tetrahedron beam computed tomography system of claim 41, wherein said first x-ray source array and said second x-ray source array perform a helical scan of said object.

53. The tetrahedron beam computed tomography system of claim 41, wherein said computer reconstructs said first and second imaging signals using a CT reconstruction algorithm.

54. The tetrahedron beam computed tomography system of claim 41, wherein said computer reconstructs said first and second imaging signals using a digital tomosynthesis algorithm.

55. A method of forming an image of an object, the method comprising:
- having a first x-ray source array, a second x-ray source array, a first detector and a second detector rotate about an axis of rotation relative to an object;
- sequentially emitting a first plurality of x-ray beams from said first x-ray source array at different positions along a first scanning direction;
- intercepting said first plurality of x-ray beams so that fan-shaped x-ray beams emanate towards said object;
- sequentially emitting a second plurality of x-ray beams from said second x-ray source array at different positions along a second scanning direction;
- intercepting said second plurality of x-ray beams so that fan-shaped x-ray beams emanate towards said object;
- having one or both of 1) a first plurality of fan-shaped x-ray beams from said first x-ray source array and after they pass through said object and 2) a first plurality of fan-shaped x-ray beams from said second x-ray source array and after they pass through said object that are received by said first detector, wherein said first detector generates a first imaging signal for each of said received first plurality of fan-shaped x-ray beams from said first x-ray source array and said received first plurality of fan-shaped x-ray beams from said second x-ray source array;
- having one or both of 1) a second plurality of fan-shaped x-ray beams from said first x-ray source and after they pass through said object and 2) a second plurality of fan-shaped x-ray beams from said second x-ray source and after they pass through said object that are received by said second detector, wherein said second detector generates a second imaging signal for each of said received second plurality of fan-shaped x-ray beams from said first x-ray source and said received second plurality of fan-shaped x-ray beams from said second x-ray source;
- receiving 1) said first imaging signals for each of said first plurality of fan-shaped x-ray beams from said first x-ray source and for each of said first plurality of fan-shaped x-ray beams from said second x-ray source and 2) said second imaging signals for each of said second plurality of fan-shaped x-ray beams from said first x-ray source and for each of said second plurality of fan-shaped x-ray beams from said second x-ray source, wherein rotation of said first x-ray source array, said second x-ray source array, said first detector and said second detector about said axis of rotation results in multiple imaging signals being reconstructed to generate a three-dimensional tetrahedron beam computed tomography image therefrom; and
- displaying said three-dimensional tetrahedron beam computed tomography image.

56. The method of claim 55, wherein said first x-ray source array comprises a first kV x-ray source array and said second x-ray source array comprises a second kV x-ray source array.

57. The method of claim 55, wherein said first x-ray source array is linear that extends along a longitudinal direction and said second x-ray source array is linear and is parallel to said first x-ray source.

58. The method of claim 57, wherein said first detector is linear and said second detector is linear and is parallel to said first detector and is perpendicular to said longitudinal direction.

59. The method of claim 58, wherein said longitudinal direction is parallel to said axis of rotation.

60. The method of claim 58, wherein said longitudinal direction is perpendicular said axis of rotation.

61. The method of claim 55, wherein said first detector is offset from a central plane that bisects said first x-ray source and is perpendicular to said rotation axis.

62. The method of claim 61, wherein said second detector is offset from said central plane that bisects said second x-ray source and is perpendicular to said rotation axis.

63. The method of claim 61, wherein said second detector is offset from said central plane.

64. The method of claim 55, wherein said first x-ray source array, said second x-ray source array, said first detector and said second detector are mounted on a rotation gantry.

65. The method of claim 64, wherein said rotation gantry rotates a full, partial rotation or multiple rotation during a scan of said object by said first x-ray source array and said second x-ray source array.

66. The method of claim 55, wherein said first x-ray source array and said second x-ray source array perform an axial scan of said object, wherein said object is stationary.

67. The method of claim 55, wherein said first x-ray source array and said second x-ray source array perform a helical scan of said object, wherein said helical scan is in part due to said object moving during said scan.

68. The method of claim 55, wherein said reconstructing of said multiple imaging signals is performed by using a CT reconstruction algorithm.

69. The method of claim 55, wherein said reconstructing of said multiple imaging signals is performed by using a digital tomosynthesis algorithm.

* * * * *